(12) United States Patent
Mertens

(10) Patent No.: US 8,163,507 B2
(45) Date of Patent: Apr. 24, 2012

(54) PROCESS FOR THE DETERMINATION OF INFLAMMATORY PROCESSES AND PHARMACEUTICAL COMPOSITIONS FOR THE TREATMENT THEREOF

(75) Inventor: Peter Rene Mertens, Aachen (DE)

(73) Assignee: Peter Rene Mertens (DE)

( * ) Notice: Subject to any disclaimer, the term of this patent is extended or adjusted under 35 U.S.C. 154(b) by 79 days.

(21) Appl. No.: 11/792,677

(22) PCT Filed: Dec. 13, 2005

(86) PCT No.: PCT/DE2005/002238
§ 371 (c)(1),
(2), (4) Date: Mar. 25, 2008

(87) PCT Pub. No.: WO2006/063567
PCT Pub. Date: Jun. 22, 2006

(65) Prior Publication Data
US 2008/0311116 A1    Dec. 18, 2008

(30) Foreign Application Priority Data
Dec. 14, 2004   (DE) .................... 10 2004 060 385

(51) Int. Cl.
*G01N 33/53* (2006.01)
*G01N 33/574* (2006.01)
(52) U.S. Cl. ......... 435/7.21; 435/7.1; 435/7.2; 435/7.23
(58) Field of Classification Search .................. 435/7.1, 435/7.2, 7.21, 7.23
See application file for complete search history.

(56) References Cited

U.S. PATENT DOCUMENTS
7,214,498 B2 * 5/2007 Nelson et al. ................ 435/7.23

FOREIGN PATENT DOCUMENTS
DE    10031122    3/2001
WO    0102556     1/2001

OTHER PUBLICATIONS

Thaiss et al. "IgA-Nephropathie,"Deutsches Aerzteblatt, Jg. 97, Heft 41, Oct. 13, 2000, pp. 2708-2711.
Goldstein et al. "Major cold shock protein of Escherichia coli," Proc. Natl. Acad. Sci. USA, vol. 87, Jan. 1990, pp. 283-287.
Didier et al. "Characterization of the cDNA encoding a protein binding to the major histocompatibility coplex class II Y box," Proc. Natl. Acad. Sci. USA, vol. 85, Oct. 1988, pp. 7322-7326.
Swamynathan et al. "Role of single-stranded DNA regions and Y-Box proteins in transcriptional regulation of viral and cellular genes," FASEB J. 12, 1998, pp. 515-522.
Morrison et al. "Chimeric human antibody molecules: Mouse antigen-binding domains with human constant region domains," Proc. Natl. Acad. Sci. USA, vol. 81, Nov. 1984, pp. 6851-6855.
Teng et al. "Construction and testing of mouse-human heteromyelomas for human monoclonal antibody production," Proc. Natl. Acad. Sci. USA, vol. 80. Dec. 1983, pp. 7308-7312.
Takeda et al. "Construction of chimeric processed immunoglobulin genes containing mouse variable and human constant region sequences," Nature, vol. 314, Apr. 4, 1985, pp. 452-454.
Kozbor et al. "The production of monoclonal antibodies from human lymphocytes," Immunology Today, vol. 4, No. 3, 1983, pp. 72-79.
Larry J. Green, "Antibody engineering via genetic engineering of the mouse: XenoMouse strains are a vehicle for facile generation of tehrapeutic human monoclonal antibodies,"Journal of Immunological Methods 231, 1999, pp. 11-23.
Mertens et al. "YB-1 Regulation of the Human and Rat Gelatinase A Genes via Similar Enhancer Elements,"J Am Soc Nephrol 10, 1999, pp. 2480-2487.
Mertens et al. "Glomerular Mesangial Cell-specific Transactivation of Matrix Metalloproteinase 2 Transaction is Mediated by YB-1,"The Journal of Biological Chemistry, vol. 272, No. 36, Sep. 5, 1997, pp. 22905-22912.
Koehler et al. "Continuous Cultures of Fused Cells Secreting Antibody of Predefined Specificity," Nature, vol. 256, 1975, pp. 495-497.
Coller et al. "Statistical Analysis of Repetitive Subcloning by the Limiting Dilution Technique with a View Toward Ensuring Hybridoma Monoclonality," Hybridoma, vol. 2, No. 1, 1983, pp. 91-96.
Mertens et al. "A Synergistic Interaction of Transcription Factors AP2 and YB-1 Regulates Gelatinase a Enhancer-dependent Transcription," The Journal of Biological Chemistry, vol. 273, No. 49, Dec. 4, 1998, pp. 32957-32965.
Dignam et al. "Eukaryotic Gene Transcription with Purified Components," Methods of Enzymology, vol. 101. 1983, pp. 582-598.
Mertens et al. "Pressure Oscillation Regulates Human Mesangial Cell Growth and Collagen Synthesis," Hypertension, vol. 32, 1998, pp. 945-952. Draper et al. "Epirgulin is More Potent thand EGF or TGFα in Promoting In Vitro Wound Closure due to Enhanced ERK/MAPK Activation," Journal of Cellular Biochemistry 89, 2003, pp. 1126-1137.
Bargou et al. "Nuclear Localization and Increased Levels of Transcription Factor YB-1 in Primary Human Breast Cancers are Associated with Intrinsic MDR1 Gene Expression,"dated Feb. 21, 1997, Nature Medicine, vol. 3, No. 4, pp. 447-450.
Van Roeyen et al. "Y-Box Protein 1 Mediates PDGF-B Effects in Mesangioproliferative Glomerular Disease,"dated Jul. 5, 2005, American Society of Nephrology.
Mertens et al; "A Synergistic Interaction of Transcription Factors AP2 and YB-1 Regulates Gelatinase A Enhancer-dependent Transcription"; J.Biol Chem 1998; vol. 273, No. 49; pp. 32957-32965.
Mertens et al; "Combinatorial Interactions of p53, Activiating Protein-2, and YB-1 with a Single Enhancer Element Regulate Gelatinase A Expression in Neoplastic Cells"; J.Bio.Chem 2002; vol. 277, No. 28; pp. 24875-24882.
Kuwano et al; "The Basic and Clinical Implications of ABC Transporters, Y-Box-Binding Protein-1 (YB-1) and Angiogenesis-Related Factors in Human Malignancies"; Cancer Sci. 2003; vol. 94, No. 1; pp. 9-14.
Notice of Rejection dated Aug. 2, 2011 for Japanese application No. 2007-545833.

* cited by examiner

*Primary Examiner* — Alana Harris Dent
*Assistant Examiner* — Anne Holleran
(74) *Attorney, Agent, or Firm* — Ohlandt, Greeley, Ruggiero & Perle, LLP

(57) ABSTRACT

A method for analyzing extracellular body fluids as to the presence of the Y-box protein YB-1 and fragments thereof, which are secreted by the cell, in order to determine inflammatory processes and malignant diseases in mammals. Also, it relates to the use of YB-1 as a marker and a kit for detecting YB-1, polypeptide fragments of YB-1, and combinations thereof. Also disclosed is a pharmaceutical composition which is used for treating inflammatory processes and malignant diseases and which contains the YB-1 protein, fragments of protein YB-1, and antibodies against the YB-1 protein and/or fragments of protein YB-1.

10 Claims, 9 Drawing Sheets

PROCESS FOR THE DETERMINATION OF INFLAMMATORY PROCESSES AND PHARMACEUTICAL COMPOSITIONS FOR THE TREATMENT THEREOF

The present invention relates to a process for the examination of extracellular body fluids for the presence of the Y box protein YB-1 and fragments thereof secreted by the cell for the determination of inflammatory processes and tumor diseases in mammals. The invention further comprises the use of YB-1 as a marker, and a detection kit for the detection of YB-1 and polypeptide fragments of YB-1 as well as combinations thereof. In addition, the invention comprises a pharmaceutical composition for the treatment of inflammatory processes and malignant diseases comprising said YB-1 protein, fragments of the YB-1 protein, antibodies against the YB-1 protein and/or against fragments of the YB-1 protein.

DESCRIPTION OF THE PRIOR ART

Inflammations are reactions of the organism, born by the connective tissue and the blood vessels of mammals, to an exterior or endogenous inflammatory stimulus with the purpose of removing or inactivating such stimulus and repairing the damage to the tissue due to the stimulus, which is generally also referred to as wound healing. Triggers for such inflammations may be mechanical stimuli, such as pressure, or foreign bodies, other physical factors, such as ionizing radiation, UV light, temperature influences, but also chemical substances, such as acids, lyes, bacterial toxins, allergens as well as pathogens, such as microorganisms, worms and insects. It is not only the variability of such inflammatory stimuli, but also the variability of the related inflammatory processes in the organism that requires an exact diagnosis of such inflammatory processes and their causes to enable a suitable therapy for controlling the inflammatory process and the related disease.

A wide variety of means is used for diagnosing the disease that belongs to the respective inflammatory process. For example, in addition to inflammatory signs that are mostly observable externally, such as reddening of the skin, evolution of heat, pain and swelling, which are palpable, visible or otherwise recognizable from outside, the results of examinations of various markers in body fluids, such as blood and urine, are also used for diagnosis. Such markers may include, for example, low-molecular weight inorganic or organic substances, proteins or cells. During such examinations, the marker substances contained in the blood or urine, for example, are examined for irregularities in comparison with their normal distribution in the blood or urine. The results may enable conclusions about the kind and cause of the disease. As examples of diseases that can be recognized by the blood picture, there may be mentioned leukemia or Pfeiffer's disease, a viral infection.

However, there are also inflammatory diseases in which the diagnosis by means of externally recognizable inflammatory signs and/or the determination of the blood picture or the urine state is not sufficient to establish an exact diagnosis about the kind or cause of the disease. As an example, there may be mentioned IgA nephropathy (IgAN, also referred to as IgA nephritis), which is a form of inflammatory mesangioproliferative glomerulonephritis. This disease is the most frequent cause of renal insufficiency, which requires regular dialysis for the patient. The indicative clinical signs required for an unambiguous diagnosis may be very different in this disease. For example, a sign that may serve as an indicative clinical sign is the occurrence of persisting microscopic hematuria or of macroscopic hematuria. In addition, the hematuria is often accompanied by proteinuria, i.e., excretion of proteins, such as albumins, $\alpha_1$ globulins and $\beta$ globulins, in substantial amounts. Although the indicative clinical signs render the presence of such an IgA nephritis very probable, the ultimate confirmation of the diagnosis requires a renal biopsy, in which a tissue specimen of the kidney is withdrawn for laboratory examinations. This rather complicated process also serves for the determination of prognostic parameters that may provide information about the further course of the disease and that help the physician to create the basis for a suitable therapy (Friedrich Thaiss and Rolf A. K. Stahl, Deutsches Ärzteblatt, Volume 1997, Issue 41, p. A2708-A2711, Oct. 13, 2000). Other inflammatory diseases that require a tissue biopsy include, for example, lupus nephritis, vasculitis or membranous glomerulonephritis. Therefore, there is still a strong need for processes for a better diagnosis and evaluation of the course of inflammatory processes or diseases that render the use of invasive methods, such as biopsy, superfluous.

Similar efforts are being made for tumor diseases. In this case too, detection methods, in part marker-based, for the extent of tumor load and the metastasis behavior of the tumors have been established, which detect alpha-fetoprotein for hepatocellular carcinoma, or carcinoembryonic antigen (CEA) and neuron-specific enolase (NSE) for bronchial carcinomas. Relapse of a tumor can in part be established early from the increase of a tumor marker to subsequently perform diagnostic examinations relating to the extent of the tumor and its localization.

Therefore, in the prior art, an intensive search is performed for both extracellular and intracellular markers that enable a quick and unambiguous diagnosis of such diseases as mentioned above. For example, DE 100 31 122 A1 describes the use of the protein YB-1, which is important for tumor progression in the cells, for the diagnosis of malignant diseases. This invention inter alia relies on the recognition that the protein YB-1 can serve its function only in the nucleus.

YB-1 belongs to a family of proteins whose members bind to certain single-stranded or double-stranded nucleic acid segments that are also referred to as Y-box. The members of this protein family occur in both prokaryotes and eukaryotes. Since it has been established in first examinations on prokaryotes that these proteins are induced in response to a cold shock (Goldstein, J. et al., Proceedings of the National Academy of Sciences USA, 1990, Vol. 87, p. 283-287), they were named "cold shock proteins". The eukaryotic YB proteins have a calculated mass of 35 kDa on average and consist of a variable N-terminus rich in arginine and alanine, a highly conserved domain of about 70 amino acids, and the alternating arrangement of 4 clusters each with basic/aromatic and acidic amino acids, respectively, in the C-terminal region. Despite their lower calculated average mass of 35 kDa, these proteins occur at a molecular weight (MW) of 50,000 to 60,000 in an SDS PAGE. The high charge differences in the C-terminal cluster are presumably the reason for the abnormal running behavior in the SDS PAGE (Dissertation by Karsten Jürchott, Humboldt Universität zu Berlin, November 1999, entitled: "Untersuchungen zur subzellulären Lokalisation und zu den Funktionen von YB-1, einem Y-Box-Protein in Säugerzellen"). The highly conserved domain that is characteristic of all YB proteins is the DNA-binding domain that obtained the designation "cold shock domain", CSD. The amino acid and nucleic acid sequences of the YB-1 protein are described, for example, in the article by Didier et al. (Proc. Natl. Acad. Sci. USA, 1988, Vol. 85, p. 7322-7326).

The class of the YB-1 protein serve a variety of tasks within the cell, due to which these proteins are interesting targets. In the review article by S. K. Swamynathan et al. (The FASEB Journal, May 1998, Vol. 12, p. 515-522), the various functions of these proteins within the cell as known to date are described. Thus, in many cell types, the YB proteins play a role in the modulation of transcription, in the modification of chromatin, in the masking of RNA during translation, in the eukaryotic redox signal pathway, in the regulation of the stress response of the cell, and in the activation of various genes. However, an involvement of the YB-1 protein in extracellular processes or an occurrence of the YB-1 protein outside the cell has been unknown to date.

DETAILED DESCRIPTION OF THE PRESENT INVENTION

The invention is based on the inventors' surprising result that the protein YB-1, which has been known only as an intracellular factor to date, is not only expressed, but also secreted by the cell in inflammatory processes and malignant diseases of cells, i.e., is secreted by the cell into the extracellular fluid of the organism. This offers the possibility for using this protein as a marker for the diagnosis of inflammatory processes and malignant diseases.

Therefore, the invention comprises an in vitro process for the determination of an inflammatory process or a malignant disease in a mammal, wherein the determination of said inflammatory process or malignant disease comprises the examination of a sample of an extracellular fluid from a mammal for the presence of the YB-1 protein and/or at least one of its fragments in the sample.

The term "determination" of an inflammatory process or a malignant disease includes the act of establishing whether an inflammatory process or a malignant disease occurs in the organism. With respect to an inflammatory process, this means, in particular, to establish whether there is a response of the organism to some exterior or endogenous inflammatory stimulus. In addition, for inflammatory diseases, this definition also includes the determination of the kind of inflammatory process from the detection of the YB-1 full-length protein, fragments of the YB-1 protein or both, which were respectively secreted by the corresponding cells into the body fluid. Further, the process according to the invention may also be used to determine the inflammatory stage in which the body of said mammal is being. With respect to the malignant diseases, above all, it can be predicted whether or not a metastasizing tumor is present. Instead of the withdrawal of a tissue specimen from the potentially tumorous tissue, the in vitro process according to the invention allows a quick and simple diagnosis in patients with suspicion of a malignant metastasizing tumor.

The process of the present invention is particularly suitable for the determination of inflammatory processes and malignant diseases in mammals. This means all mammals whose body cells secrete YB-1 and/or fragments of YB-1 in inflammatory processes or metastasizing tumor diseases. Humans are examples of a mammal whose cells secrete YB-1 and fragments of YB-1 in inflammatory processes or malignant diseases. This is illustratively demonstrated in Example 6 for the secretion of YB-1 protein by isolated primary macrophages. Other cell types that secrete YB-1 include mesangial cells, B and T lymphocytes, tumor cells, such as HepG2 cells, or MonoMac-6 cells in acute myelosis.

Due to the fact that the YB-1 protein described in the present invention and the fragments of the YB-1 protein are secreted by the cell, and are thus present as secreted YB-1, the detection of YB-1, protein fragments of YB-1 or combinations thereof in an extracellular body fluid is possible. The withdrawal of body fluid is simpler than, for example, the withdrawal of a tissue specimen, which is required for ultimately ascertaining the diagnosis, for example, in IgA nephritis. At the same time, the process of the present invention enables early diagnosis of a disease without withdrawing tissue specimens and without the need for a preceding localization diagnosis in tumor diseases.

"Extracellular body fluids" according to the invention refers to blood, urine, lymph, plasma, serum, sweat, nasal secretion, vaginal secretion, wound exudate, sputum, pus, semen, stool or cerebrospinal fluid. Among these, urine, sweat, nasal secretion, vaginal secretion, wound exudate, sputum, pus, semen and stool can be collected simply during secretion from the body or obtained by preparing a smear. Blood, plasma, serum, lymph and cerebrospinal fluid can be obtained from the subject's vascular system by needle aspiration, wherein blood must be centrifuged after withdrawal to obtain blood plasma free of blood corpuscles. For the user, the detection of YB-1 proteins, fragments of YB-1 protein or a combination thereof from urine is the simplest and quickest possibility to determine the inflammatory process or malignant disease. The urine can then be examined continuously for YB-1 proteins, protein fragments of YB-1 protein or combinations thereof.

The extracellular YB-1 (rows "LPS/sup." in FIG. 3) is distinguished from nuclear YB-1 (rows "NE" in FIG. 3) by its slightly higher mobility in a polyacrylamide gel, as can be seen from FIG. 3 (Example 2) (with different anti-YB-1 antibodies directed against different epitopes of YB-1). This difference results from the fact that the protein is modified, wherein an alternative secretory pathway has been detected, i.e., YB-1 is not modified by the cell's ER or Golgi apparatus. In addition, fragments of the protein that change depending on the activity of the disease are detected, such as in active mesangioproliferative IgA nephritis with detection of fragments of sizes 28, 23, 16 and 8 kDa (see FIG. 6), and in tumor diseases with enhanced detection of an approximately 16 kDa fragment in the serum (see FIG. 11).

When YB-1 protein secreted by the cells is detected, the present invention makes use of the fact that YB-1 protein is cleaved into smaller fragments after or during its secretion from the cell. Since, in inflammatory kidney diseases, such as IgA nephritis, or in kidney graft rejection, the smaller fragments are formed in a relatively disease-specific way, a disease activity can be concluded from the specific detection of the fragments in a body fluid, such as urine.

The "secretion pattern" results from the different occurrences of YB-1, its fragments and combinations thereof. In addition to full length YB-1, which occurs at 52 kDa in a Western blot, smaller fragments having sizes of 8 kDa, 16 kDa, 23 kDa, 28 kDa, 30 kDa, 32 kDa and 35 kDa occur. Depending on the course of an inflammatory process or a malignant disease, the distribution and amount of the occurring fragments may change. Further, other YB-1 fragments can be established which may occur in inflammations or malignant diseases that have not yet been examined completely. The sizes of the fragments can deviate slightly upwards or downwards depending on how the detection method employed is performed. Therefore, the invention also includes fragments having a molecular weight that deviates by up to ±5 kDa from the molecular weight as determined in the Examples in this invention. YB-1 and fragments of YB-1 can be detected, inter alia, by means of the antibodies mentioned in Table 1.

Alternatively to the detection of the full-length YB-1 and the fragments of YB-1 by means of a Western blot as described in Example 1, the determination of the secretion pattern may also be effected by HPLC. As compared to Western blotting, HPLC enables a better quantification of the detected fragments. Further details relating to HPLC and other methods of protein analytics can be found in the book "Bioanalytik" by F. Lottspeich and H. Zorbas (Spektrum Akademischer Verlag, May 1998, 1st Edition, ISBN 3-8274-0041-4). Other methods used in protein analytics are known to the skilled person. For example, there may be mentioned staining tests, such as the biuret assay, the Lowry assay, the bicinchonic acid assay (BCA assay), the Bradford assay; spectroscopic methods, which include radioactive labeling, the iodination of proteins and mass spectrometry in addition to UV and fluorescence measurements; enzymatic tests; and immunological detection techniques; chromatographic separation methods; electrophoretic methods; capillary electrophoresis; sequence analysis; and X-ray structural analysis.

For example, a YB-1 secretion pattern with occurrence of fragments of sizes 8, 16 and 23 kDa in the urine to date has been observed exclusively in diseases accompanied by inflammation of the mesangial cells in the renal corpuscles. Within the scope of kidney graft rejections, it has been detected by immunohistochemistry that the characteristic cell infiltrates of monocytes and lymphocytes express considerable amounts of YB-1. Due to the secretion pattern in the urine and the results with MM-6 cells upon ATP and LPS stimulation, it can be considered that inflamed cells secrete YB-1 and its fragments during the rejection reaction and therefore, they can be detected in the urine.

Full length YB-1 and a 30 kDa YB-1 fragment can be detected in considerable amounts in the serum of healthy subjects. If the serum of patients having different metastasizing tumor diseases is examined by Western blotting with a polyclonal antibody directed against the full-length YB-1 protein and with a monoclonal antibody, a YB-1 fragment band of 16 kDa can be detected additionally in all tumor patients examined (n=15; FIG. 11). The 16 kDa fragment cannot be detected in the three healthy subjects tested and the septic patient S2. Corresponding results were obtained with different polyclonal antibodies against full length YB-1.

Therefore, the process of the present invention additionally comprises the evaluation of the examination results obtained in the above examination to determine a secretion pattern of the YB-1 protein and its fragments in the sample. Depending on the type of inflammatory process and the stage that such inflammatory process is in, the amounts and sizes of the individual protein fragments of extracellular YB-1 obtained in the cleavage are clearly distinguished from the size distribution of the individual protein fragments of YB-1 that are formed in other inflammatory processes. Thus, the "secretion pattern" of YB-1 and its protein fragments in a rejection reaction upon a kidney transplantation, as can be seen in FIG. 9 (Example 5), is clearly distinguished from the YB-1 secretion pattern in an IgA nephritis as represented in FIGS. 6 and 7 (Example 4). This means that the user of the process according to the invention can determine the kind, cause and stage that the inflammatory disease is in from the distribution of the YB-1 and the YB-1 protein fragments. Therefore, the process of the present invention further comprises the step of comparing the previously determined secretion pattern with secretion patterns established from calibration series for inflammatory processes. The secretion pattern determined thereby always includes the full-length YB-1 protein itself. The calibration series can be established from multiple measurements on different patients, as illustrated in an exemplary manner in Examples 4, 5 and 7.

In FIG. 8, in a patient with IgA nephritis, it can be seen from the YB-1 urine diagnostics that the kidney function returns to normal over a period subsequent to the disappearance of the low-molecular weight bands. Due to the detection of the low-molecular weight band, for example, a decision for the treatment for immunosuppression can be derived. In addition, the detection of the 16 kDa fragment in the serum enables the diagnosis or evaluation of the course of tumor diseases (FIG. 11, Example 7).

The results shown in FIGS. 6 and 7 make it clear that the secretion pattern appears almost identical in different patients. FIG. 6 shows the results of the examinations of two patients both of which exhibit a progredient course of IgA nephritis. The YB-1 secretion pattern for these patients is also characterized by fragments at 28, 23, 16 and 8 kDa in the gel in addition to the full-length YB-1 at 52 kDa. It may be mentioned that the kDa values stated within the scope of the description of the invention relate to the position of the bands in the gel. In FIG. 7, the urine examination result for YB-1 with spontaneous urines from 12 patients with bioptically ascertained IgA nephritis has been performed. The patients' data are sorted by the level of serum creatinine when applied in the gel, and the course of the creatinine concentration in the following two years is stated. A secretion pattern in which smaller fragments having sizes of 23, 16 and 8 kDa occur in addition to the full-length YB-1 protein and the 28 kDa fragment (lanes 10 and 11) is accompanied by a progression of the disease up to the terminal renal insufficiency with obligatory dialysis. Therefore, the secretion patterns for YB-1 established by such measurements on patients with a known course of the disease can be used as a calibration series for the determination of such inflammatory processes in other patients.

As can be seen further from the results in FIG. 9 (Example 6), the detection of the YB-1 protein and its fragments as a marker substance for the detection of inflammatory processes, an organ rejection in this Example, is possible clearly earlier than detection with conventionally used markers. As can be seen from FIG. 9, the smaller YB-1 protein fragment at 26 kDa can be seen in patient A already before the rise of the concentration of Granzyme B or MIG, which are employed as early markers of the rejection reaction. The monoclonal antibody used here (AB 4) recognizes the mentioned fragment.

The results of the experiments performed also allow the conclusion that the application of the method of the present invention in inflammatory processes in the kidney, as in an IgA nephritis, is independent of the extent of a proteinuria, which is normally recurred to in kidney diseases for the more exact diagnosis of the inflammatory process. Thus, the present invention represents an effective early-warning system for the diagnosis of inflammatory processes and malignant diseases in the mammal organism.

The detection of the extracellularly occurring YB-1 protein, the at least one YB-1 protein fragment or combinations thereof is effected by processes known in the prior art. These include, for example, protein determination by means of staining tests, enzymatic activity tests, immunological and spectroscopic methods. A survey of these techniques is found, for example, in the book "Bioanalytik" by F. Lottspeich and H. Zorbas (Spektrum Akademischer Verlag, May 1998, 1st Edition, ISBN 3-8274-0041-4). Immunological detection with antibodies, for example, is suitable for detecting the YB protein. After the separation by Western blotting of the proteins contained, for example, in the urine, polyclonal antibodies or monoclonal antibodies are used that are directed against different segments of the full-length YB-1 protein, which may therefore also be used for the detection of protein fragments of YB-1. The detection of YB-1 and fragments thereof by means of antibodies is of advantage because this immunological detection is very specific and very sensitive. In the prior art, for example, in DE 100 31 122 A1, antibodies are described that are directed against intracellular YB-1 protein, which becomes accessible to immunological examinations only after lysis of the cells from the tissue specimens.

The process of the present invention is suitable, in particular, for the determination of inflammatory processes in a mammal organism. Such an inflammatory process may be a rejection reaction after a transplantation or an inflammatory disease. The inflammatory disease is selected from the group consisting of nephrological diseases, asthma, chronic obstructive lung diseases, rheumatoid arthritis, vasculitis, diabetes mellitus, cancer, leukemias, sepsis, pancreatitis, multiple sclerosis, psoriasis and dermatitis. Depending on its stage, each disease is attributed a specific secretion pattern for the protein YB-1, YB-1 protein fragments or combinations thereof. The process is suitable, in particular, for the determination of nephrological diseases.

The nephrological disease is selected from the group consisting of glomerulonephritis, especially IgA nephritis, interstitial nephritis, pyelonephritis, lupoid nephritis, radiogenic nephritis, vascular nephropathy and cystic kidneys. Examples of different secretion patterns in different diseases (for example, IgA nephritis and organ rejection) or different stages of disease, such as in IgA nephritis, which shall be discussed in an exemplary manner in the following Examples, become evident from the Examples.

As shown in the Examples, the process of the present invention is also suitable for the determination of malignant diseases. Such malignant diseases include tumors selected from the group consisting of solid tumors, such as pancreatic carcinoma, rectal carcinoma, gastric carcinoma, colon carcinoma, mammary carcinoma, malignant melanoma, kidney cell carcinoma, laryngeal carcinoma, ovarian carcinoma, prostatic carcinoma, bronchial carcinoma and leukemias, such as acute myeloic, acute lymphocytic, chronic myeloic and chronic lymphatic leukemias.

The invention further comprises the use of YB-1 or at least a fragment thereof or a combination thereof for determining an inflammatory process in a mammal. Due to the fact that the secretion of YB-1 can be observed in all kinds of inflammatory processes and malignant diseases, YB-1 or at least one of its fragments or the combination thereof is particularly suitable as a marker for inflammatory and malignant diseases in the body of a mammal. In particular, immunological techniques making use of specific antibody/antigen binding are suitable for the detection of the YB-1 protein, at least one of its fragments or combinations thereof.

For the detection of the YB-1 protein, at least one of its fragments or combinations thereof, the invention also provides a detection kit which serves for the determination of an inflammatory process in a mammal. Said detection kit comprises at least one antibody suitable for the detection of the YB-1 protein and/or at least one fragment thereof. By means of the detection kit, the secretion pattern for YB-1 is established and compared with the existing calibration series for inflammatory processes or malignant diseases. The early diagnosis and determination of said inflammatory process or malignant disease enables a suitable therapy for the patient to be developed early.

The means for the detection of the protein YB-1 comprise antibodies, wherein said antibodies may be both monoclonal and polyclonal antibodies that can specifically bind to at least one antigenic determinant of the YB-1 protein or its fragments. Antibodies suitable for the process of the present invention are set forth in Table 1. The antibodies include, but are not limited to, IgG, IgA, IgE, IgM and IgD antibodies.

Such kits may contain both buffers for the storage of said antibodies and reagents which protect said antibodies from proteolytic degradation.

Due to the surprising result that the YB-1 protein and fragments of the YB-1 protein are secreted by the cell, possible medical applications arise that are based on the interaction of the secreted YB-1 protein or its fragments with other cell factors or receptors. Therefore, the invention further includes a pharmaceutical composition for the treatment of inflammatory processes and malignant diseases comprising an agent selected from the group containing YB-1 protein, fragments of YB-1 protein, antibodies against YB-1 protein and/or against fragments of YB-1 protein.

The inventors have found out that the secreted YB-1 influences inflammatory processes and cell proliferation by paracrine and autocrine effects. Thus, the inventors were able to show in several experiments that YB-1 binds to receptors of the NOTCH family. NOTCH receptors are a family of transmembrane receptors involved in the regulation of many differentiation processes in the cell, such as the differentiation of stem cell populations during muscular development or hematopoiesis. In addition, an anti-apoptotic effect of the activated human variant of the NOTCH-1 receptors in T cells is known, whereby the development of certain cell populations is regulated. Several connections between NOTCH-dependent and NF-κB-dependent signal pathways in the activation of immunocompetent cells under the influence of proinflammatory stimuli (TNF-α/bacterial lipopolysaccharides) have been established. By applying recombinant YB-1, the activity of YB-1 can be enhanced, and a cell differentiation can be initiated that is important, for example, in proliferate diseases, such as neurodermitis. The proliferation of a cell can be inhibited and a differentiation achieved thereby. In contrast, the application of antibodies binding secreted YB-1 can inhibit the recruitment of inflammatory cells (immigrating monocytes/macrophages). This is desirable, for example, to avoid rejection reactions in transplants, but also in the prevention of atherosclerosis or intimal hyperplasia upon coronary intervention and stent insertion. Other applications relate to the treatment of tumor diseases in which a differentiation of the cells leads to inhibition of growth.

Thus, the inventors could show in an experiment with a keratinocyte culture (Example 8) that YB-1 and antibodies against YB-1 influence the differentiation of the cells. Further, it could be shown that YB-1 binds to TGF-β-binding protein (LTBP) and thereby causes the release of further inflammatory mediators, such as TGF-β.

Therefore, the present invention also relates to a pharmaceutical composition which preferably comprises monoclonal antibodies, it being of particular advantage for medical application if the monoclonal antibodies are chimerized or humanized. Humanized antibodies have a lower immunogenic effect than the corresponding non-humanized antibodies. In humanization, either only the variable domains or only the hypervariable regions with the antigen binding site are of non-human origin and are introduced in otherwise human antibody scaffolds. A wide variety of experiments for the preparation of chimerized or humanized antibodies have been known in the prior art (Morrison et al., Proc. Natl. Acad. Sci. USA, 1985, Vol. 81, p. 6851; Takeda et al., Nature, 1985, Vol. 314, p. 452; Cabilly et al., U.S. Pat. No. 4,816,567; Teng et al., Proc. Natl. Acad. Sci. USA, 1983, Vol. 80, p. 7308-7312; Kozbor et al., Immunology Today, 1983, Vol. 4, p. 7279; Green, L. L., Journal of Immunological Methods, 1999, Vol. 231 (1-2), p. 11-23).

The monoclonal antibodies used in the present invention are selected from the group of monoclonal antibodies prepared from hybridoma cell lines as represented in Table 1. A monoclonal antibody of the hybridoma cell line having the accession No. DSM ACC 2703 is preferred.

In a particular embodiment of the pharmaceutical composition, the antibodies, the YB-1 protein, the fragments of the YB-1 protein or a combination thereof are immobilized on biologically compatible implants. Wound healing, for example, by bowel anastomosis or hernia repair, is to be accompanied by as high as possible a collagen expression. The differentiation of the immigrating cells, such as macrophages, and their interaction with resident and immigrating fibroblasts influences the phenotype of the cells and the collagen expression pattern. By coating biologically compatible materials with the antibodies of the present invention or recombinant YB-1, the wound healing can be influenced directly. Such biologically compatible implants can be selected from the group comprising plastic nets, wound plasters, scaffolds of hydroxyapatite or polycaprolactone, to mention just a few.

The pharmaceutical composition of the present invention is particularly suitable for the treatment of inflammatory processes and malignant diseases, wherein said inflammatory process may be a rejection reaction of the mammal upon transplantation or an inflammatory disease.

Said inflammatory disease may be a nephrological disease, asthma, chronic obstructive lung disease, intimal hyperplasia, rheumatoid arthritis, atherosclerosis, vasculitis, diabetes mellitus, sepsis, pancreatitis, multiple sclerosis, psoriasis, colitis and dermatitis.

Said malignant disease may be a solid tumor, such as pancreatic carcinoma, rectal carcinoma, gastric carcinoma, colon carcinoma, mammary carcinoma, malignant melanoma, kidney cell carcinoma, laryngeal carcinoma, ovarian carcinoma, prostatic carcinoma, bronchial carcinoma and leukemia, such as acute myeloic, acute lymphocytic, chronic myeloic and chronic lymphatic leukemias.

Said nephrological disease may be glomerulonephritis, especially IgA nephritis, interstitial nephritis, pyelonephritis, lupoid nephritis, radiogenic nephritis, vascular nephropathy and cystic kidneys.

The pharmaceutical composition of the present invention may be administered in a form suitable for oral use, for example, as a tablet, capsule, aqueous or oily solution, suspension or emulsion; for topical use, which includes transmucosal and transdermal use, it may be administered, for example, in the form of a cream, ointment, gel, aqueous or oily solution or suspension, ointment or plaster. It may also be administered by inhalation, for example, as an aerosol. It is similarly suitable for parenteral use (including intravenous, subcutaneous, intramuscular, intravascular or infusion), for example, as a sterile aqueous or oily solution or suspension. If the site of the inflammatory process or the malignant disease can be localized exactly, a suitable method of administration may be the direct injection at this site of the solution which contains said pharmaceutical composition.

Generally, the pharmaceutical composition of the present invention is formulated conventionally by means of usual excipients (vehicles) using standard techniques known to the skilled person.

For the oral administration of the pharmaceutical composition of the present invention, it is generally provided in the form of a tablet, capsule or as an aqueous solution or suspension.

Tablets for oral use may include active components admixed with pharmaceutically acceptable excipients, such as inert diluents, disintegrating agents, binders, bulking agents, glidants, sweeteners, flavors, colorants and preservatives. Suitable inert diluents include sodium or calcium carbonate, sodium or calcium phosphate and lactose. Suitable disintegrating agents include, for example, amylum and alginic acid. Binders include, for example, starch and gelatin, whereas the glidants, if present, include magnesium stearate, sebacic acid or tallow. If desired, the tablets may be coated with a material like monostearin or glycerol 1,3-distearate, for example, in order to retard absorption in the gastrointestinal tract. Capsules for oral use include solid gelatin capsules, in which the active pharmaceutical component is admixed with a solid diluent, and soft gelatin capsules, in which the active pharmaceutical component of the present invention is admixed with water or an oil, such as peanut oil, liquid paraffin or olive oil. For the intramuscular, intraperitoneal, subcutaneous or intravenous use of the pharmaceutical composition of the present invention, it is generally provided as a sterile aqueous solution or suspension adjusted to a suitable pH and isotonicity. Suitable aqueous carriers include adjuvants, such as Ringer's solution and isotonic sodium chloride. Aqueous suspensions may include suspending agents, such as cellulose derivatives, sodium alginates, polyvinylpyrrolidine-2-one and tragacanth, and a wetting agent, such as lecithin. Suitable preservatives include, for example, ethyl and n-propyl p-hydroxybenzoic acid.

DESCRIPTION OF FIGURES

In FIG. 1A, the induction of YB-1 (band at 52 kDa) secretion was effected by the monocytic cell line MM-6 at an LPS concentration of 1.0 ng/ml in lane 4 (row 1 serves as a control, no addition of LPS (−)). Lower ($10^{-2}$ to $10^{-1}$ ng/ml) and higher (10 to $10^4$ ng/ml) concentrations of LPS led to no secretion or only to a low one. At the same concentration of LPS, 1 ng/ml, secretion of the macrophage migratory inhibitory factor (MIF) was observed, and actin could also be detected. This demonstrates the specificity of the secretion mechanism and the fact that this is not cell lysis. In FIG. 1B, the LPS concentration range of between 0.25 and 10 ng/ml was tested with MM-6 cells. It is found that YB-1 is secreted at an LPS concentration of from 1.0 to 7.5 ng/ml and can be detected with the polyclonal peptide antibody generated against the C terminal of the protein.

Similarly as in FIG. 1.

In FIG. 6, 3 samples from two patients (A and B) suffering from IgA nephritis and as proteinuria of above 1.5 g/d recovered at intervals of several weeks are applied. They all show an almost identical secretion pattern of YB-1 and proteolytic fragments of YB-1. Further details relating to the results are found in Example 4.

EXAMPLES

Figure 1:
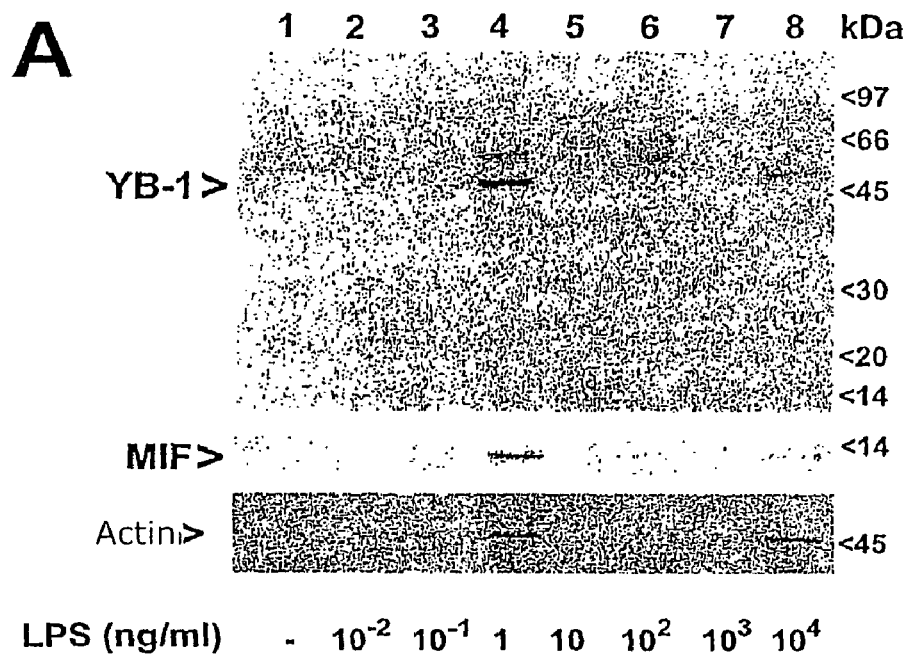
FIGS. 1A and 1B show the detection of YB-1 and its fragments by means of polyclonal antibodies directed against the C-terminal of the protein (Mertens P. R., Alfonso-Jaume M. A. et al., J. Am. Soc. Nephrology, 1999, Vol. 10, p. 2480-2487) upon induction of monocytic MM-6 cells with lipopolysaccharide (LPS) solutions of different concentrations.
Figure 1:
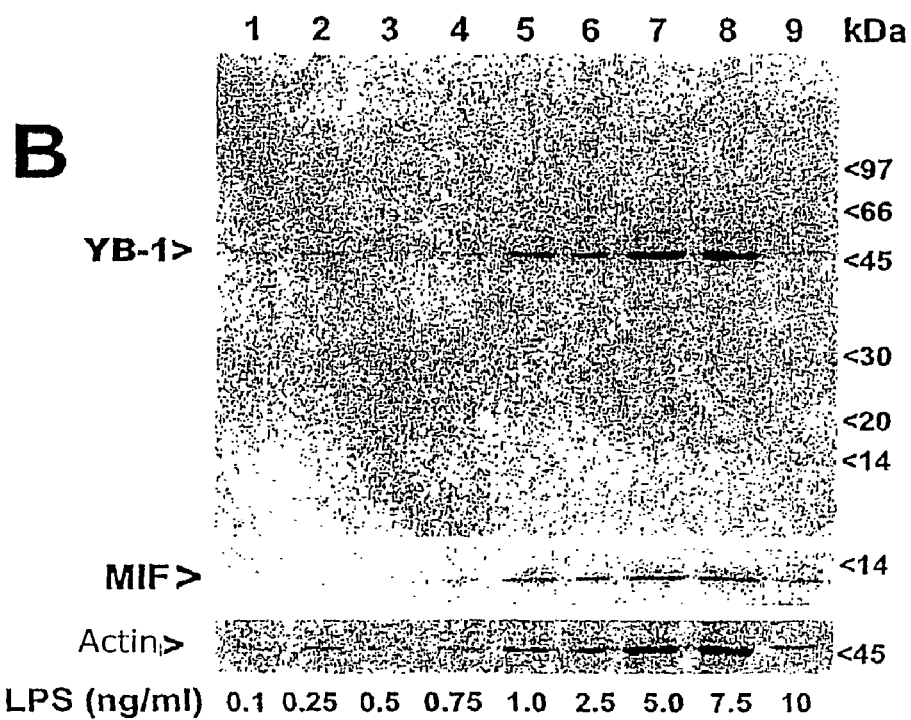

In the following, the antibodies used in the Examples are summarized in a Table. In particular, it is shown against what portion of the full-length YB-1 protein or against what fragment(s) of the YB-1 protein the antibody is directed.

TABLE 1

| Antibody designation | Antibody (AB) type (monoclonal or polyclonal) | AB is directed against (what fragments and/or full-length YB-1) | Source |
|---|---|---|---|
| AB1 | polyclonal | C terminal of YB-1 protein | Martens P. R. et al., J. Am. Soc. Nephrology, 1999, Vol. 10, p. 2480-2487 |
| AB2 (anti-hare HRP-conjugated F(ab')2 fragment) | polyclonal | second antibody | Amersham Biosciences UK Limited, Buckinghamshire, UK |
| AB3 (polyclonal hare antibody) | polyclonal | full length YB-1 protein | Mertens P. R. et al., The Journal of Biological Chemistry, 1997, Vol. 272, No. 36, p. 22905-22912 |
| AB4 | monoclonal | full length YB-1 | Hybridoma cell line "Deutschland" (deposited with the DSMZ under Accession No. DSM ACC 2703) |
| AB5 (anti-mouse antibody (PI-2000)) | polyclonal | second second antibody | Amersham Biosciences UK Limited, Buckinghamshire, UK |
| AB6 (polyclonal hare antibody against HA tag) | polyclonal | HA-YB-1 fusion protein (MW 54 kDa) | Y-11 Santa Cruz Biotechnology Inc., Santa Cruz, California, USA |
| AB7 (polyclonal goat antibody) | polyclonal | N terminal of YB-1 protein | A-16X, Santa Cruz Biotechnology Inc., Santa Cruz, California, USA |
| AB8 | monoclonal | full length YB-1 | Hybridoma cell line "Italien" |
| AB9 | monoclonal | AB9 has a lower affinity for the full-length YB-1 protein and a 26 kDa fragment in the serum. No detection of smaller YB-1 fragments, such as 16 or 23 kDa | Hybridoma cell line "Großbritannien" |

Example 1

Detection of Secreted YB-1 and Its Fragments Upon Stimulation of the Monocytic Cell Line MM-6 with Lipopolysaccharides (LPS)

Recovery of Microvesicles from MM-6 Monocytic Cells and Detection of YB-1

MM-6 monocytic cells grow as a suspension culture in RPMI 1640 medium containing 10% (v/v) FCS (fetal calf serum), 2 mM L-glutamine, 100 μg/ml streptomycin and 100 U/ml penicillin-G. After a washing operation in phosphate-buffered saline (PBS), the cells are taken up in RPMI medium containing Lipumine™ (PAA Laboratories GmbH, Pasching, Austria) without FCS addition, and counted. In Eppendorf vessels, $2 \times 10^6$ MM-6 cells are incubated at 37° C. with LPS and adenosine triphosphate (1 mM) (both from Sigma Aldrich, St. Louis, USA) in the concentrations as stated in FIGS. 1 and 2 for 4 hours. Subsequently, the medium with the cells is centrifuged for 10 min at 330×g for the cells to sediment, and the supernatant is then centrifuged again for 15 min at 2200×g. The supernatant after the second centrifugation is admixed with ice cold trichloroacetic acid for the precipitation of the proteins (including the microvesicles) and stored over night at −20° C., followed by centrifuging for 30 min at 33,000×g and discarding the supernatant. The pellet is washed once with ice cold non-denatured ethanol (70%) and dried in a vacuum centrifuge.

Subsequently, the dried sediment is taken up in 25 μl of distilled water. After the addition of 25 μl of denaturing buffer, it is separated by electrophoresis in an SDS polyacrylamide (SDS-PA) gel (12.5%), and YB-1 and fragments of YB-1 are detected with the antibodies mentioned below under the item "Antibody detection" (Mertens P. R. et al., J. Am. Soc. Nephrology, 1999, Vol. 10, p. 2480-2487) in a Western blot (see below). In addition to the full-length YB-1 (52 kDa), fragments of YB-1 having sizes of 35, 32, 28 and 16 kDa were also detected.

Western Blot Analysis
Solutions Employed:
Lower (separating) gel buffer (4×): 1.5 M Tris-HCl, pH 8.8
Acryl/bisacryl (30%): 29.2 g acrylamide, 0.8 g bisacrylamide, 70 ml H₂O Upper (stacking) gel buffer (4×): 0.5 M Tris-HCl, pH 6.8
SPS (10%): 10 g of SDS in 90 ml of $H_2O$
APS (10%): 1 g of ammonium peroxodisulfate in 9 ml of $H_2O$
Electrophoresis buffer (10×): 30 g of Tris-HCl, 144 g of glycine, 10 g of SDS, bring to 1000 ml with $H_2O$, adjust all to pH 8.3
Sample buffer (4×): 2.4 ml of $H_2O$, 2.4 ml of lower gel buffer, 2.0 ml of glycerol, 2.0 ml of SDS (10%), 200 µl of bromophenol blue solution (1%), 40 µl of EDTA solution (0.5 M), 1 ml of β-mercaptoethanol
Transfer buffer: 3.03 g of Trizma base, 14.4 g of glycine, 200 ml of methanol, bring to 2000 ml with $H_2O$
TTBS solution: 1916 ml of $H_2O$, 60 ml of NaCl solution (5 M), 20 ml of Tris solution (1 M, pH 8), 4 ml of Tween-20 solution (25%).

The proteins were separated by electrophoresis, transferred to a nitrocellulose membrane and detected with anti-YB-1 antibodies as follows (see the list below under the item "Antibody detection"): First, a 12.5% SDS PA gel was cast into the BioRad Minigel System. For 4 lower gels (corresponding to about 25 ml), the following solutions were mixed successively: $H_2O$ 8 ml, lower gel buffer (4×) 6.25 ml, acryl/bisacryl (30%) 10.4 ml, SDS (10%) 250 µl, TEMED 12.5 µl, APS (10%) 125 µl.

Subsequently, the lower gel while still liquid was pipetted immediately between the glass plates of the Minigel system until the level of the liquid was 1 cm below the upper edge of the glass plate. The remaining space was filled with water, and polymerization was performed at room temperature for 45 minutes.

For 4 lower gels, the following solutions were mixed successively: $H_2O$ 6.1 ml, lower gel buffer (4×) 2.5 ml, acryl/bisacryl (30%) 1.3 ml, SDS (10%) 100 µl, TEMED 10 µl, APS (10%) 50 µl.

The excess water between the glass plates was decanted, and the glass gap was filled with the liquid lower gel. The comb was inserted immediately, and the lower gel was polymerized at room temperature for 45 minutes. In the meantime, the samples from the cell extracts or after centrifugation of the supernatant are prepared. 10 µl of sample was mixed with 10 µl of denaturing sample buffer (Laemmle) and incubated in a water bath at 95° C. for 3-5 minutes. The combs are removed from the polymerized gel, and the chamber filled with electrophoresis buffer (1× concentration). Subsequently, each sample is briefly centrifuged, the sample wells are prewashed with a pipette, each sample is applied to a sample well and separated by electrophoresis at 150 volts for about 1 hour.

During the electrophoresis, the preparations for the transfer are made. Thus, the transfer buffer was prepared and precooled at 4° C. For each gel, a nitrocellulose membrane and double the number of Whatman papers were cut to size. After the electrophoresis, the gels were taken from the chamber, the nitrocellulose membrane and Whatman paper were wetted in transfer buffer and stacked without bubbles in the following order: Whatman paper, nitrocellulose membrane, gel, Whatman paper. For the transfer, the nitrocellulose membrane is faced towards the anode in the transfer chamber, the chamber is filled with transfer buffer, an ice block is inserted for cooling, and blotting is performed at 100 volts for 1 hour.

Antibody Detection

After the transfer, the membranes are washed in TTBS solution for 3×10 minutes, blocked in 2% BSA solution (dissolved in TTBSA) for 2 hours at room temperature, and again washed in TTBS for 3×10 minutes. The membranes are subsequently incubated with the first antibody at a dilution of 1:2000 over night at 4° C. Different anti-YB-1 antibodies are employed (see the list below). After a further washing operation, the membranes are incubated with the second antibody (see the list below).

The following combination of antibodies ([first antibody]: [second antibody]) are employed to detect YB-1 and fragments of YB-1:

Polyclonal hare antibody against the YB-1 C terminal (AB1) (Mertens P. R. et al., J. Am. Soc. Nephrology, 1999, Vol. 10, p. 2480-2487): anti-hare HRP-conjugated F(ab')2 fragment (AB2) (Amersham Biosciences UK Limited, Buckinghamshire, UK) from donkey, incubated at RT for 2 hours at a dilution of 1:5,000.

Polyclonal hare antibody against the full length YB-1 protein (AB3) (Mertens P. R. et al., The Journal of Biological Chemistry, 1997, Vol. 272, No. 36, p. 22905-22912): anti-hare HRP-conjugated F(ab')2 fragment (AB2) (Amersham Biosciences UK Limited, Buckinghamshire, UK) from donkey, incubated at RT for 2 hours at a dilution of 1:5,000.

Monoclonal anti-YB-1 antibody (AB4 and AB8): anti-mouse antibody (AB5) (PI-2000, Amersham Biosciences UK Limited, Buckinghamshire, UK) from donkey, incubated at RT for 2 hours at a dilution of 1:20,000. The monoclonal antibodies "Deutschland" (AB4) and "Italien" (AB5) against the full length YB-1 protein recombinantly prepared in bacteria were generated by immunizing mice and isolating spleen lymphocytes after 2 booster injections with the recombinant protein according to the following protocol and fusing them with hybridoma cells.

Preparation of Monoclonal Antibodies

Immunization: BALB/c mice at an age of 8 weeks were immunized with purified antigen (rYB-1 proteins, see Mertens et al., The Journal of Biological Chemistry, 1997, Vol. 272, No. 36, p. 22905-22912). The dosage is 150 µg/mouse. For the first immunization, the antigens are emulsified in complete Freund's adjuvant (CFA; Sigma) (water-in-oil emulsion, Hurn and Chantler, 1980) and injected into the mice subcutaneously in a volume of 300 µl. Before the immunization, blood is withdrawn from the tail vein of the mice (preimmune serum). 4 weeks after the first immunization, blood is withdrawn from the mice (immune serum). The antibody titers in these sera are determined in a semiquantitative enzyme immunoassay (slot blot). Mice having a high antibody titer are immunized 6-8 weeks after the first immunization and again 2 weeks later (booster immunization). Thus, 100 µg of rYB-1 in PBS are injected into the animals intravenously. The fusion is effected 3-5 days after the last immunization.

Preparation of the splenocyte suspensions for obtaining splenocytes: After cervical dislocation, the spleen is withdrawn from the mice under sterile conditions and carefully plucked apart with 2 pairs of tweezers in a Petri dish in HBSS (Hank's buffered salt solution). Cell lumps and residues of connective tissue are removed by filtration through a fine wire mesh. Subsequently, the cells are washed three times in HBSS (centrifugation for 10 min at 200×g at room temperature). For the cloning of the hybridomas, recombinant IL-6 (100 U/ml, Roche) is employed.

Cell fusion: For the cell fusion, a modified protocol of the method originally described by Köhler and Milstein (Köhler and Milstein, Biotechnology, 1992; Vol. 24, p. 524-526) is used. $10^8$ washed splenocytes from an immunized mouse and 2 to $5×10^7$ 8-azaguanine-resistant myeloma cells (X63-Ag8/653) are mixed in a 50 ml centrifugation tube. The myeloma cells are grown 10 days before in large cell culture flasks (225 $cm^2$). Subsequently, their cell number is determined in a Neubauer counting chamber. The tube is filled with GKN medium (8 g/l NaCl, 0.4 g/l KCl, 1.77 g/l Na$_2$HPO$_4$, 0.69 g/l NaH$_2$PO$_4$, 2 g/l glucose) and centrifuged at room temperature at 200×g for 10 min. The supernatant is aspirated. Over a period of 1 min, 0.5 ml of 50% PEG solution (Sigma) is added dropwise. The pellet is resuspended by carefully tapping. In order to dilute the PEG, 5 ml of GKN medium is added after 90 seconds over a period of 5 min. After a resting phase of 10 min, large lumps are dissolved by carefully pipetting with a 10 ml pipette. The cell suspension is subsequently diluted in HAT medium (medium with hypoxanthine, aminopterine and thymidine for the cultivation of cell hybrids, DMEM (Gibco), 2 mM L-glutamine, 5×10$^{-5}$ M β-mercaptoethanol, 2% (v/v) 50×HAT, 1% (v/v) non-essential amino acids, 10% (v/v) fetal calf serum, 100 μg/ml streptomycin and 100 U/ml penicillin) and distributed to 6 microtitration plates (96 wells). The cell density is about 1×10$^5$ per well in a volume of 100 μl. At one week intervals, the hybridomas are supplied with HAT medium. After about 2 weeks, the majority of the hybridomas has expanded and comprises a cell number of about 5×10$^3$-10$^4$. At this time, the supernatants are tested with a dot-blot enzyme immunoassay for their content of specific antibodies. For this purpose, 100 μl/well of each of the supernatants is removed from the microtitration plates and employed. Positive tested hybridomas are expanded.

Cloning according to the limiting dilution principle: In order to ensure the monoclonality of an antibody-producing clone, the limiting dilution method described by Coller and Coller (Hybridoma, 1983; Vol. 2, p. 91-96) suggests itself. By means of a Neubauer cell chamber, the cell number of the clones is determined and the cell culture diluted with medium, so that statistically only one cell is distributed to every second well of a 96 well plate. The cultures are again expanded, and after about 2 weeks, the supernatants from these cultures are again tested in an enzyme immunoassay (Western blot, ELISA) for the production of specific antibodies. Positive clones are expanded, characterized in more detail and frozen in liquid nitrogen for preservation. For freezing, the hybridoma cells are harvested, centrifuged off, resuspended at a cell density of 1×10$^6$ cells/ml in ice cold freezing medium (DMEM with 10% (v/v) DMSO, 20-30% (v/v) fetal calf serum) and stored in nitrogen.

Isotyping of the "Deutschland" antibody (AB4) provided the result that it belongs to the IgG2b subclass. The antibodies with designations "Italien" (AB8) and "Großbritannien" (AB9) were prepared in the same manner.

The detection is effected by means of an "enhanced chemiluminescence" reaction (ECL™, Amersham Biosciences UK Limited, Buckinghamshire, UK), followed by X-ray film exposure.

Results:

In FIG. 1A, the induction of the secretion of full length YB-1 (52 kDa) becomes clear when 1 ng/ml LPS is added (lane 4). Lower concentrations (10$^{-2}$ to 10$^{-1}$ ng/ml) and higher concentrations (10 to 10$^4$ ng/ml) lead to no secretion or only to a low one, as can be seen, for example, at an LPS concentration of 10$^4$ ng/ml (lane 8).

A further test row in a more limited concentration range of from 0.1 to 10 ng/ml (FIG. 1B) shows that full length YB-1 is secreted by the MM6 cells at LPS concentrations of from 1.0 to 7.5 ng/ml. When the membrane from the Western blotting is incubated longer with the antibodies, a constitutive expression of full length YB-1 can be seen also at low LPS concentrations (0.25 to 0.75 ng/ml) (FIG. 2). In addition, a secretion of YB-1 cleavage products becomes clear at LPS concentrations of between 1.0 and 7.5 ng/ml. The cleavage products of YB-1 have sizes of 35, 32, 28 and 16 kDa.

Figure 2:
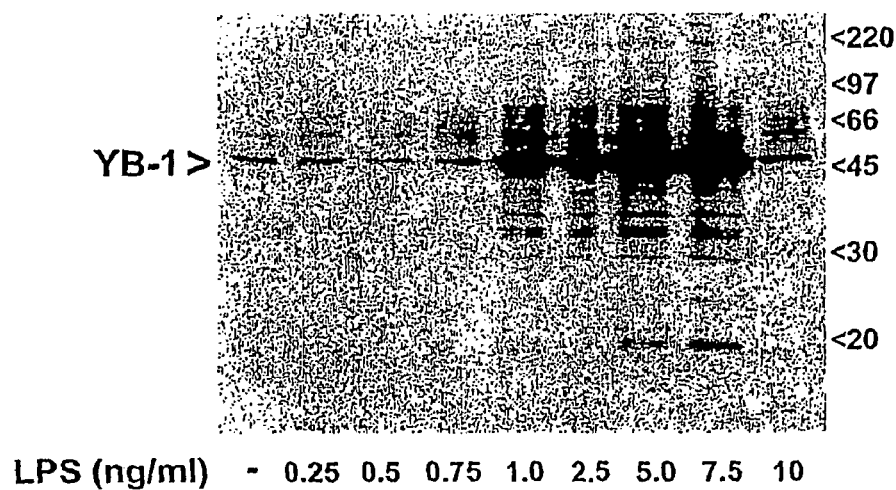
FIG. 2 shows the results of a Western blotting with prolonged antibody exposure. Thus, a constitutive secretion of YB-1 can be detected even at lower LPS concentrations (0.25 to 0.75 ng/ml). In addition, at LPS concentrations of from 1 to 7.5 ng/ml, secretion of YB-1 cleavage products having molecular weights of 35, 32, 28 and 16 kDa is observed.

In FIG. 1, it is also shown that the macrophage migratory inhibitory factor (MIF) and actin are present at LPS concentrations of 1 ng/ml (FIG. 1A) and 1 ng/ml to 7.5 ng/ml, respectively (FIG. 1B). This demonstrates the specificity of the secretion mechanism and the fact that the detected YB-1 is not derived from lysed cells.

Example 2

Comparison of the Molecular Weight (MW) of Intracellularly Expressed and Secreted YB-1

In this experiment, the differences in molecular weight between YB-1 recombinantly prepared in *E. coli* (rYB-1), nuclear YB-1 (NE) and YB-1 secreted upon LPS stimulation of MM-6 cells (LPS/sup.) are examined.

The description of the experimental set-up for the LPS stimulation of MM-6 cells and the determination of the secreted YB-1 are found in Example 1. The preparation of recombinant YB-1 and the isolation of nuclear YB-1 are effected by the method as described in the articles by Mertens et al., J. Biol. Chem., 1997, Vol. 272, p. 22905-22912; Mertens P. R. et al., J. Biol. Chem., 1998, Vol. 273, p. 32957-32965. The Western blotting subsequently performed with the samples of nuclear YB-1, recombinant YB-1 and YB-1 secreted upon LPS stimulation is performed according to the description for Example 1. The antibodies used in the Western blotting are directed, on the one hand, against the C terminal (anti-C (AB1); see above, Mertens P. R. et al., J. Am. Soc. Nephrology, 1999, Vol. 10, p. 2480-2487);

the N terminal (anti-N (AB7), anti-YB-1 antibody from Santa Cruz employed at a dilution of 1:2000); and the full-length YB-1 protein (anti-w (AB3; see above Mertens P. R. et al., The Journal of Biological Chemistry, 1997, Vol. 272, No. 36, p. 22905-22912) (for further details, see Example 1). The recovery of nuclear cell extracts is described in more detail in the following.

Recovery of Nuclear Cell Extracts (NE):
Solutions Employed:
Hypotonic buffer: 10 mM HEPES pH 7.9, 1.5 mM MgCl$_2$, 10 mM KCl, 0.2 mM PMSF, 0.5 mM DTT, 1 mM sodium orthovanadate.
Buffer with low salt conc.: 20 mM HEPES pH 7.9, 25% (v/v) glycerol, 1.5 mM MgCl$_2$, 20 mM KCl, 0.2 mM EDTA, 0.2 mM PMSF, 0.5 mM DTT, 1 mM sodium orthovanadate.
Buffer with high salt conc.: 20 mM HEPES pH 7.9, 25% (v/v) glycerol, 1.5 mM MgCl$_2$, 1.0 M KCl, 0.2 mM EDTA, 0.2 mM PMSF, 0.5 mM DTT, 1 mM sodium orthovanadate.
Dialysis buffer: 20 mM HEPES, 20% (v/v) glycerol, 0.1 M NaCl, 0.2 mM EDTA, 0.2 mM PMSF, 0.5 mM DTT.

The recovery of nuclear extracts is adapted from the method described by Dignam et al. (Methods Enzymol., 1983; Vol. 101, p. 582-598). The cells are sown in 250 ml cell culture flasks and cultured in complete RPMI medium with 10% FCS to a confluency of 80%. The medium is decanted, the cells are washed once with ice cold PBS and subsequently detached carefully with a cell scraper in 10 ml of ice cold PBS. The following steps are always performed on ice or at 4° C.: centrifuging the cell suspension for 10 minutes at 3,000 revolutions per minute (rpm), decanting the supernatant and taking up the cell pellet in 5 pellet volumes of hypotonic buffer (see above). The suspension is again centrifuged at 3,000 rpm for 5 minutes. The pellet is again taken up in hypotonic buffer (3 pellet volumes), incubated on ice for 10 minutes and centrifuged at 4,000 rpm for 15 minutes. The supernatant is discarded after the centrifugation, the sediment is taken up in buffer with a low salt concentration (½ pellet volume), and buffer with high salt concentration (⅓ of the total volume) is added carefully by pipetting. Subsequently, the extracts are shaken for 30 minutes each and centrifuged at 14,000 rpm. In the meantime, dialysis tubes are boiled in 0.05 M EDTA and soaked in water. After the centrifugation, the supernatant is pipetted into the dialysis tubes and dialyzed in 2 liters of precooled dialysis buffer over night at 4° C. with constant stirring. On the next morning, the dialysis buffer is changed and dialyzed for another 2 hours. Subsequently, the samples are aliquoted, shock-frozen with liquid nitrogen and stored at −80° C.

Figure 3:
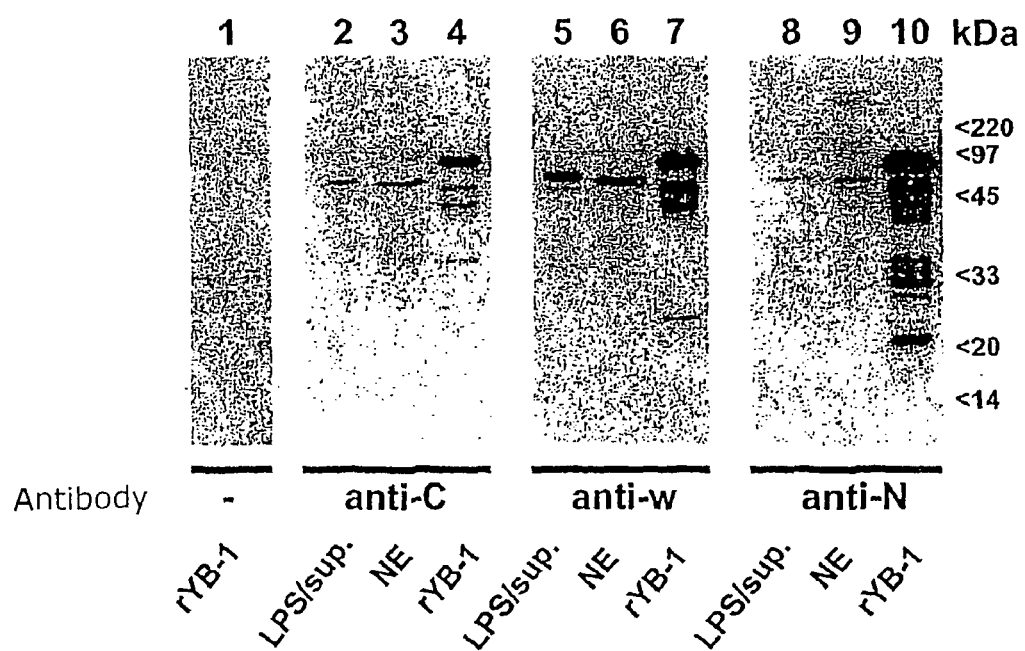
FIG. 3 shows the differences in molecular weight between YB-1 recombinantly prepared in *E. coli* (rYB-1), nuclear YB-1 (NE) and YB-1 secreted upon LPS stimulation of MM-6 cells (LPS/sup.) in a Western blot. The antibodies employed are directed, on the one hand, against the C terminal (anti-C), the N terminal (anti-N) and the full-length YB-1 protein (anti-w). The first row in the gel serves as a negative control (i.e., no first antibody was used). Further details relating to this experiment can be found in Example 2. A lower mobility of secreted YB-1 (lanes 1, 5 and 8) as compared to YB-1 of nuclear origin (lanes 3, 6 and 9) is found. The prokaryotically prepared YB-1 (rYB-1) is distinguished from eukaryotically prepared YB-1 (LPS/sup.) not only by its molecular weight of 46 kDa, but also by the fact that it can be detected as a higher-molecular weight band (88 kDa). The higher-molecular weight band can be accounted for most probably by homomultimerization. In addition, fragments having sizes of 38, 36, 35, 33 and 22 kDa can be detected. With the antibody prepared against the full-length YB-1 protein, in addition, a 25 kDa fragment can be detected with recombinant YB-1 (lane 7).

Results:

The first row in the gel of the Western blot shown in FIG. 3 serves as a negative control (i.e., no primary antibody was used). A lower mobility of secreted YB-1 (lanes 1, 5 and 8) is found as compared to YB-1 of nuclear origin (lanes 3, 6 and 9). The prokaryotically prepared YB-1 (rYB-1) is distinguished from eukaryotically prepared YB-1 (LPS/sup.; 52 kDa) not only by its molecular weight of 46 kDa, but also by the fact that it can be detected as a higher-molecular weight band (88 kDa) (lanes 4, 7 and 10), most probably because of homomultimerization. In addition, fragments having sizes of 38, 36, 35, 33 and 22 kDa can be detected. With the antibody prepared against the full-length YB-1 protein, in addition, a 25 kDa fragment can be detected with recombinant YB-1 (lane 7).

Regarding the difference between secreted and intracellular YB-1, the inventors currently only know that secreted YB-1 is not in a glycosylated form as described for secretion products of the classical pathway. There are data which shed some more light on the secretion pathway of YB-1 (not shown). According to current knowledge, the secretion is effected actively through ABC transporters, which very probably can be attributed to the alternative secretion pathway. In addition, when FIG. 3 is analyzed, it is noted that the secreted YB-1 is larger by about 5 kDa than the nuclear YB-1 protein (about 57 kDa) and exists not only as a full-length protein, but also in fragments. As can be seen in FIG. 3, intracellular YB-1 exists as a double band at 50 and 52 kDa (see, for example, lane 9).

Example 3

Detection of YB-1 Secreted in Microvesicles and Fragments of YB-1 After Stimulation of a Conditionally HA-YB-1 Expressing Mesangial Cell Line with the Platelet-Derived Growth Factor PDGF-B The following Example shows that cells of a conditionally HA-YB-1 expressing mesangial cell line will secrete YB-1 and fragments of YB-1 upon stimulation with PDGF-B. The experiment additionally demonstrates that the secreted YB-1 protein is not a different member of the cold shock family of proteins, to which YB-1 belongs.

For this purpose, this Example uses primary mesangial cells from rats (Mertens et al., Hypertension, 1998, Vol. 32, p. 945-952). They grow in RPMI 1640 medium added with 10% fetal calf serum, 2 mM L-glutamine, 1 mM Na pyruvate, non-essential amino acids, 5 mg/l insulin, 3.4 µg/l sodium selenite, 2.8 mg/l transferrin, 100 µg/ml streptomycin and 100 U/ml penicillin at 37° C. under an $H_2O$-saturated atmosphere containing 5% $CO_2$.

To induce the cells for the secretion of YB-1, the cells are grown in 75 cm2 culture dishes in the presence of hygromycin (200 µg/ml) and geneticin (400 µg/ml) to 80% confluency. Prior to stimulation with PDGF-B, the cells are treated with MCDB medium (Sigma, St. Louis, Mo., USA) for 24 h in order to discontinue growth. PDGF-B is added to the RMPI medium to a final concentration of 50 ng/ml. After the cultivation, the cells are detached from the bottoms of the cell culture flasks with PBS without calcium and magnesium/EDTA (1 mM) and transferred into a sterile 50 ml Falcon tube, followed by centrifuging at 1000 rpm for 10 min and taking off the supernatant. The cell pellet is resuspended in 5 ml of PBS, the cell number is counted in a Neubauer chamber, and the cells are again centrifuged at 1000 rpm for 10 min. The cell pellet is taken up in RPMI medium without added serum, so that the cell number is $5\times10^5$ cells/100 µl of medium. 200 µl is pipetted into an Eppendorf vessel and incubated in a thermoblock shaker at 37° C. with PDGF-B (20 ng/ml PDGF-B).

Figure 4:
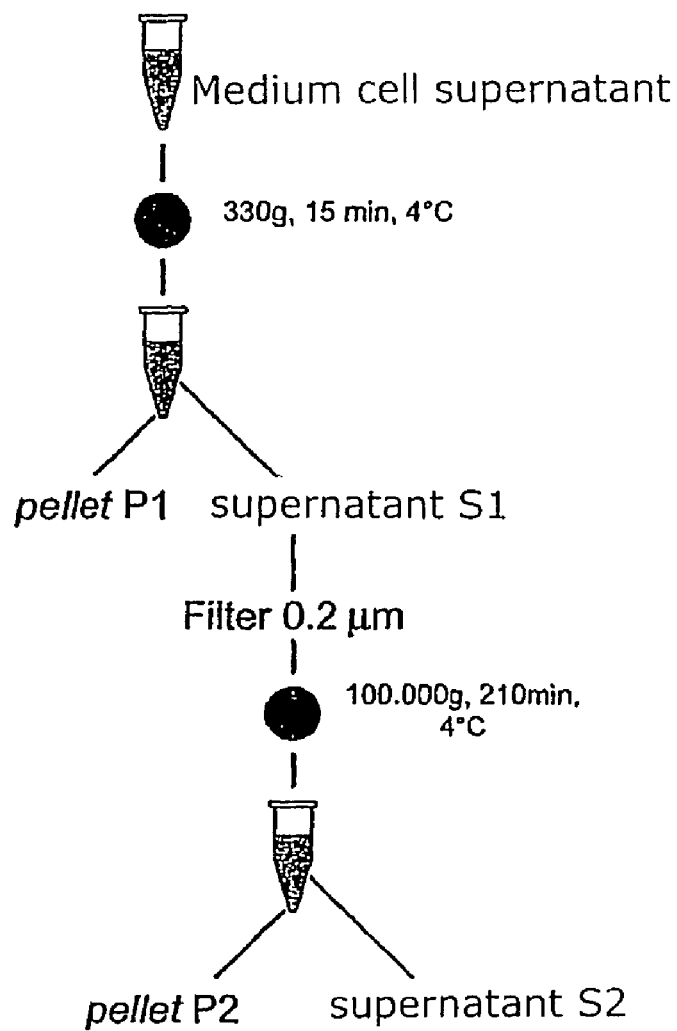
FIG. 4 shows a schematic representation of the process for the isolation of YB-1 and its fragments from the microvesicles containing YB-1 and having been secreted by the mesangial cells induced by PDGF-B. Further details relating to the experiment can be found in Example 3. P1 represents sediment 1, which is obtained after the first centrifugation of the cell supernatant after 1 h or 4 h upon cytokine incubation and which mainly contains cells, high-molecular weight components and cell fragments. S1 represents the cell supernatant remaining after the first centrifugation, which is subsequently centrifuged to obtain microvesicles. S2 represents the supernatant obtained thereby, and P2 represents the second sediment, which contains the YB-1 protein and its fragments in microvesicles.
Figure 5:
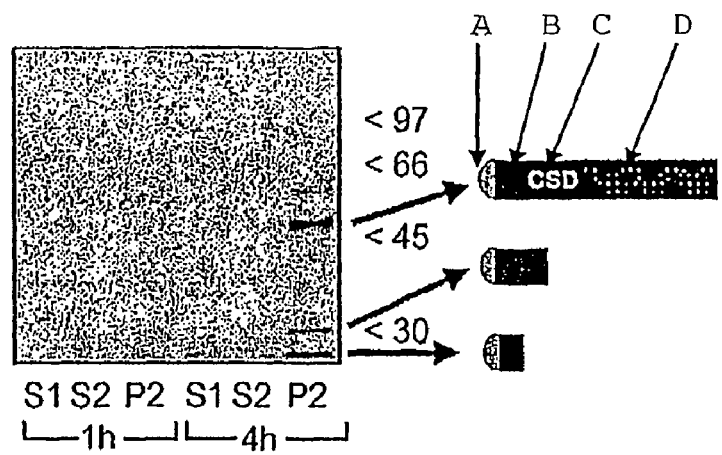
FIG. 5 represents the results of the immunological detection of the YB-1 secreted by mesangial cells in a Western blot. The meaning of abbreviations S1, S2 and P2 are found in the description relating to FIG. 4. The domain marked by the letter "A" is the N-terminal domain of secreted YB-1. "B" represents the domain of secreted YB-1 that is rich in arginine and alanine, "C" represents the cold-shock domain (CSD) of the secreted YB-1, and "D" represents the alternating positively and negatively charged segments at the C terminal of secreted YB-1. In this experiment, a YB-1 protein provided with a hemagglutinin tag that is expressed by the rat mesangial cells is detected in a Western blot with an anti-HA antibody. This approach excludes that the secreted protein is a different member of the cold shock family of proteins to which YB-1 belongs. For further details relating to the experiment, see Example 3.

After 4 hours of incubation time, the Eppendorf vessels are centrifuged at 4° C. at 330×g for 15 min to sediment the cells. 50 µl of the supernatant (S1) is preserved for LDH measurement. The remaining supernatant is passed through a 0.2 µm filter (Qualilab, Merck, Bruchsal, Germany) and centrifuged at 100,000×g for 210 min. The supernatant (S2) and the sediment (P2) are separately taken up in denaturing Laemmli buffer, and all samples are separated in a 10% SDS-PA gel (see FIG. 5). The secreted microvesicles are contained in sediment P2. A schematic representation of the above mentioned steps, which lead to the recovery of microvesicles in the medium, is shown in FIG. 4. The immunological detection of the YB-1 protein in a subsequent Western blotting (for details of the Western blotting, see Example 1) is effected by means of an anti-HA antibody (AB6).

Example 4

Detection of YB-1 and its Cleavage Products in the Urine of Patients with Progredient IgA Nephritis Examples 4 to 5 and 7 to 8 illustrate the correlation of the secretion of the YB-1 protein and fragments of the YB-1 protein by the cells with the clinical picture of the patients examined. These examples show the possibility of utilizing patterns of the secretion of YB-1 and its fragments by the cell for the unambiguous assignment to an inflammatory process in a patient. Thus, the origin and course of inflammatory diseases in the patient can be determined better.

Figure 6:
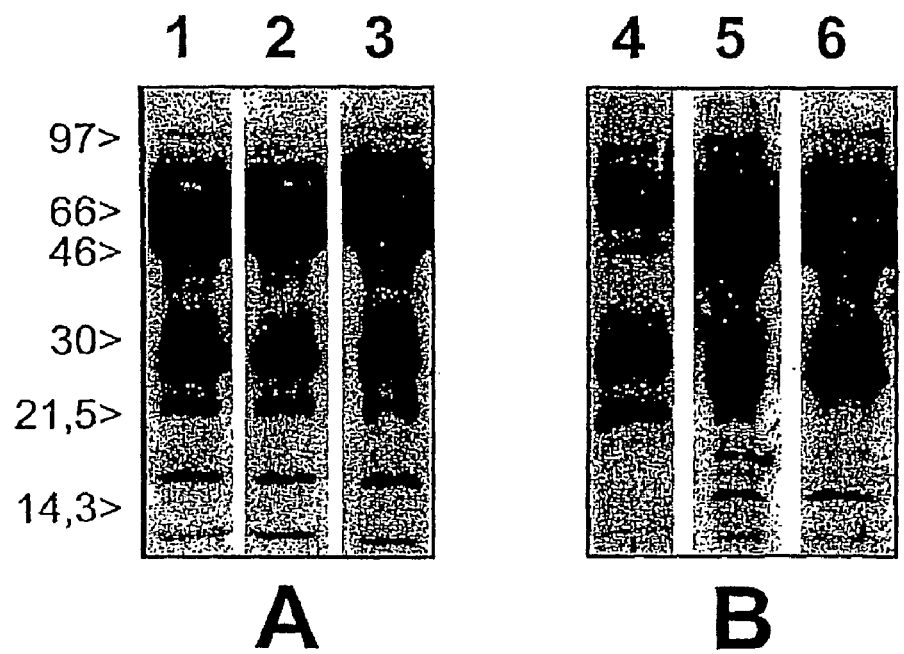
FIG. 6 shows the immunological detection of the protein YB-1 (band at 52 kDa) and its proteolytic fragments having sizes of 28, 23, 16 and 8 kDa recovered from the urine of patients, effected with a polyclonal antibody directed against the full YB-1 protein.

In this Example, the secretion pattern of YB-1 and fragments of YB-1 in a progredient IgA nephritis is shown for 2 patients (FIG. 6). The detection of YB-1 and its proteolytic fragments in a Western blot (further details of the Western blot are found in Example 1) is effected with a polyclonal antibody prepared against the full YB-1 protein (AB3) (Mertens P. R. et al., The Journal of Biological Chemistry, 1997, Vol. 272, No. 36, p. 22905-22912).

In two selected patients with proteinuria, which is an accompanying effect of all kidney diseases, of above 1.5 g/d (designated with A and B in FIG. 6), a characteristic secretion pattern for YB-1 is found in these immunological examinations. The YB-1 protein labeled with the polyclonal antibody and its proteolytic fragments occur in both patients in a similar characteristic band pattern in the gel, wherein protein bands can be observed at molecular weights of 52, 28, 23, 26 and 8 kDa (see FIG. 6, lanes 1 and 4). The band at 52 kDa represents the full-length protein YB-1. By the multimerization of YB-1 with itself and other smaller fragments of YB-1, bands with molecular weights of above 52 kDa also occur.

While the course of the disease remained the same in the patients, these results were sequentially confirmed at intervals of about 3 months by examining further spontaneous urine samples (FIG. 6, lanes 2 and 3 for patient A and 5 and 6 for patient B). In all cases, almost always the same band pattern occurred in the gel, which indicates the constant secretion of YB-1 and its proteolytic fragments.

Figure 7:
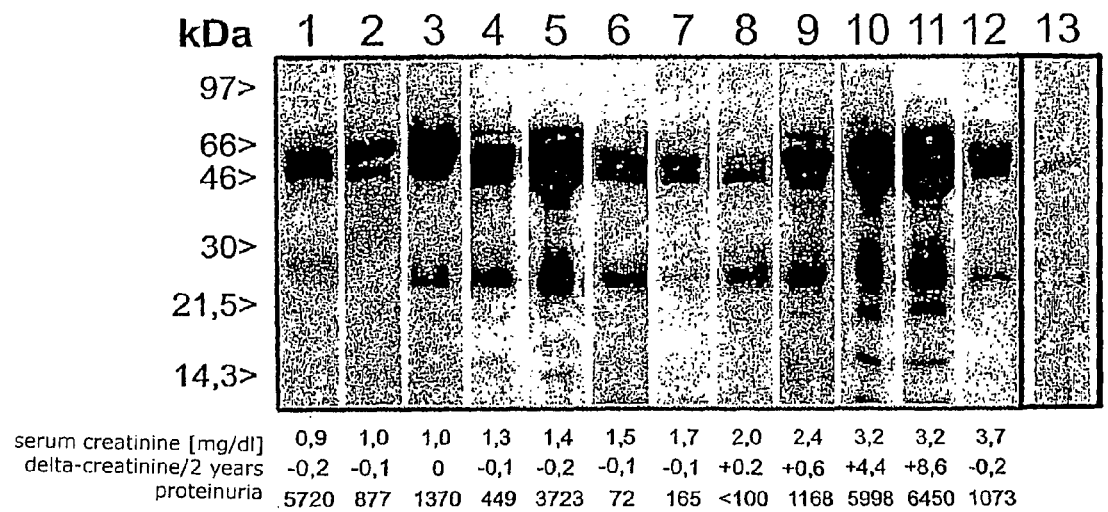
FIG. 7 shows a gel with twelve urine samples obtained from patients suffering from IgA nephritis and sorted by increasing creatinine values. In the immunological detection with an antibody directed against the full length YB-1 protein, it is noteworthy that fragments with molecular weights of 28, 23, 16 and 8 kDa can also be detected in addition to the full-length YB-1 protein at 52 kDa. After the preservation of samples, the patients were evaluated with respect to their clinical course, and the rise in serum creatinine level was stated. While the renal function was stable in most patients, a progression towards terminal renal failure and obligatory dialysis occurred in the two patients in whom the 23, 16 and 8 kDa YB-1 fragments had been detected. In addition, it was noted that the detection of YB-1 is obtained independently of the extent of proteinuria.

FIG. 7 shows a gel of 12 urine samples obtained from patients with IgA nephritis. The stated concentrations for serum creatinine below the individual lanes of the gel indicate the current kidney function while the delta creatinine values in the serum indicate how the kidney function develops. The course of the concentration change of the creatinine concentration was observed over 2 years in the patients, and the arrangement of the samples on the gel for the patients has been ranged by increasing creatinine concentrations. In the immunological detection with an antibody directed against the full length YB-1 protein (AB-3) (Mertens P. R. et al., 1997, The Journal of Biological Chemistry, Vol. 272, No. 36, p. 22905-22912), it is noted that fragments having molecular weights of 28, 23, 16 and 8 kDa can also be detected in addition to the full-length YB-1 protein at 52 kDa. After sample preservation, the patients were evaluated with respect to their clinical course, and the rise of serum creatinine was stated. While the kidney function is stable in most patients, a progression up to terminal renal failure and obligatory dialysis occurred in the two patients in whom the 23, 16 and 8 kDa YB-1 fragments had been detected. In addition, it was noted that the detection of YB-1 is obtained independently of the extent of proteinuria, as can be seen from comparative data relating to proteinuria below the image of the gel. As a control, the urine sample of one of the two patients with progredient renal insufficiency (lane 10) is incubated exclusively with the second antibody in lane 13. The lower molecular weight bands cannot be observed in this case.

Figure 8:
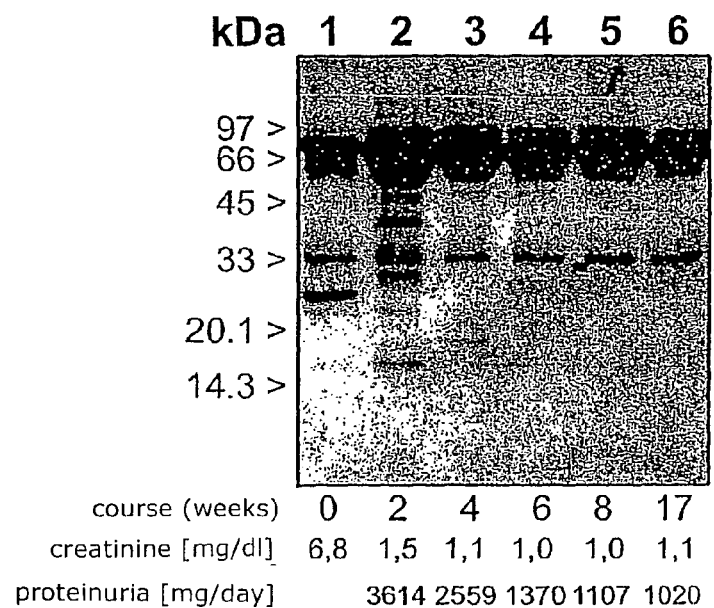
FIG. 8 shows in an exemplary manner the course in a patient with bioptically ascertained IgA nephritis in whom the YB-1 secretion pattern in the urine changed in the course of several weeks. It was noted that the low-molecular weight bands disappear, and a recovery of renal function occurs. At the time of acute renal failure (time 0), the patient was treated with immunosuppression.

FIG. 8 shows in an exemplary manner the course in a patient with bioptically ascertained IgA nephritis in whom the YB-1 pattern in the urine changed over weeks. It is noted that low-molecular weight bands disappear, and a recovery of renal function occurs. At the time of acute renal failure (time 0), the patient was treated with immunosuppression.

Example 5

Detection of YB-1 Protein and its Protein Fragments as Indicators of Acute Kidney Graft Rejection The monoclonal antibody "Deutschland" (AB4) was used for detecting YB-1 in a Western blotting. This monoclonal antibody does not recognize the smaller fragments at 8, 16 and 23 kDa. After the kidney transplantation has been effected, the urine samples are collected sequentially in the 6 patients examined (A-F). In the patients A and B, designated as AR in FIG. 9, there is a rejection reaction (AR) ascertained by biopsy. In the patients C and D, there is neither a rejection reaction nor any other complications (No AR). In the patients E and F, although there were no rejection reactions, there were other complications (comp., ø AR), such as peritonitis and catheter-associated sepsis. Parallel to the determination of the presence of YB-1 and its fragments, cytokines and other marker proteins for rejection reactions were also determined.

Figure 9:
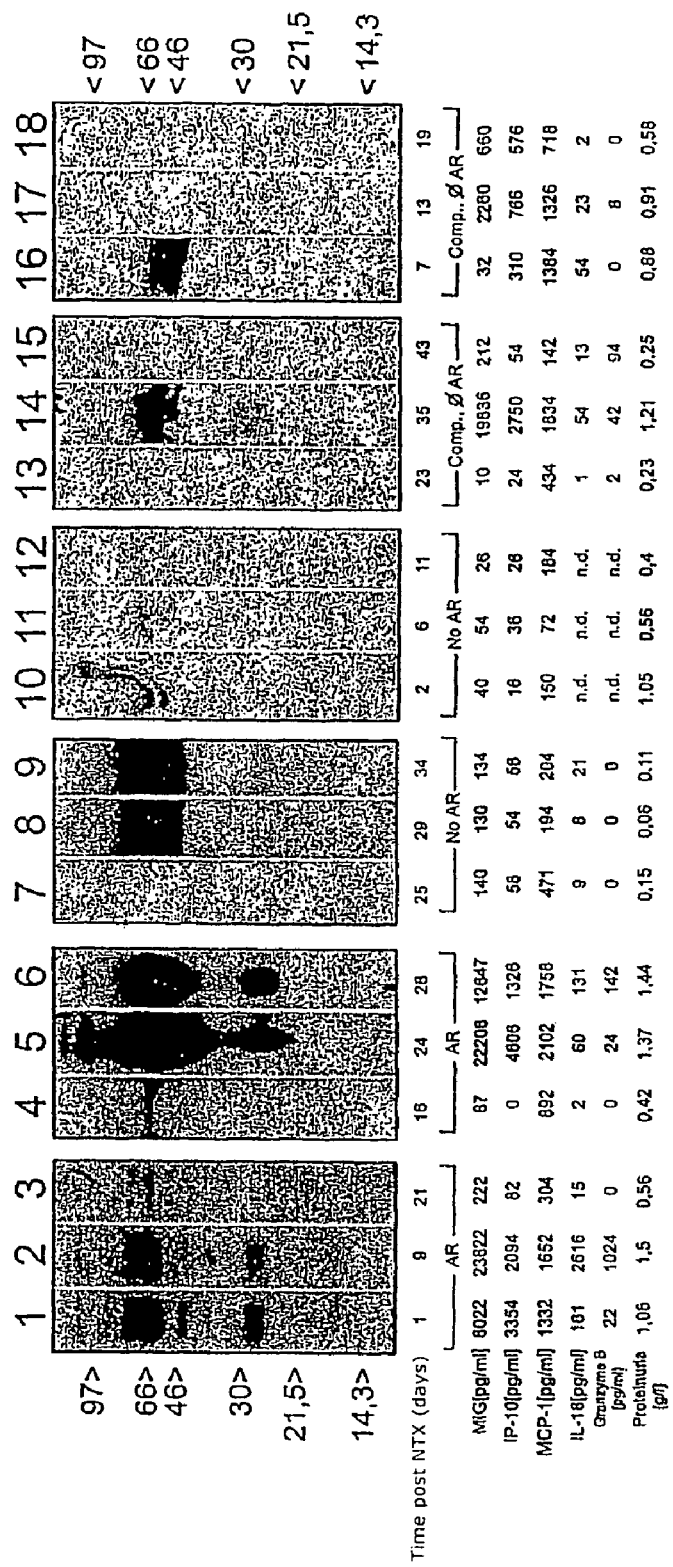
FIG. 9 shows the immunological detection of secreted YB-1 and its protein fragments in an acute kidney graft rejection reaction from the urine of 6 patients by means of a monoclonal antibody directed against YB-1. After the kidney transplantation had been performed, the urine samples were collected sequentially in the 6 patients examined (A-F). In the patients A and B, designated as AR in FIG. 9, there is a rejection reaction (AR) ascertained by biopsy. In the patients C and D, there is neither a rejection reaction nor any other complications (No AR). In the patients E and F, although there were no rejection reactions, there were other complications, i.e., infectious ones (comp., ø AR). Parallel to the determination of the presence of YB-1 and its fragments, cytokines and other marker proteins for rejection reactions were also determined (MIG in pg/ml; IP-10 in pg/ml; MCP-I in pg/ml; IL-18 in pg/ml; Granzyme B in pg/ml; proteinuria in g/l).

The results in FIG. 9 show that the reaction of the body after the transplantation is clearly reflected in the secretion profile of YB-1 and its protein fragments. As can be seen in patient A in FIG. 9, the smaller fragments (MW of about 27 kDa) are detectable already before Granzyme B, which has been evaluated as an early marker of the rejection reaction, has significantly risen. This results additionally shows that the detection of YB-1 and its fragments is independent of the extent of proteinuria.

The preceding Examples show that the analysis of the YB-1 secretion pattern offers the physician in charge a quick possibility to determine the inflammatory processes and the cause of such inflammatory processes.

Example 6

Secretion of YB-1 by Monocytic Cells and Macrophages Upon Stimulation with LPS

Figure 10A:
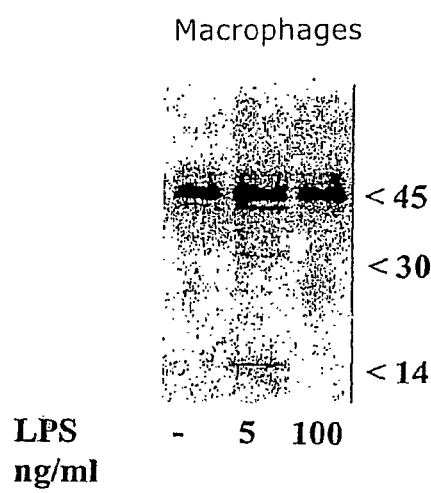
FIG. 10A shows the results of an experiment in which primary human monocytes and macrophages are isolated from the blood of a healthy subject and incubated with LPS. After stimulation with LPS in a concentration of 5 ng/ml, full-length YB-1 as well as a 16 kDa fragment could be detected in the serum-free supernatant.

As can be seen in FIG. 10A, primary human monocytes and macrophages obtained from the blood of healthy donors by means of buffy coats according to a standard protocol also begin to secrete YB-1 upon incubation with LPS. In the blot, a polyclonal antibody (AB3) prepared against the full YB-1 protein was employed for detection.

Example 7

Detection of YB-1 and Fragments of YB-1 in Connection with Malignant Diseases

Figure 11:
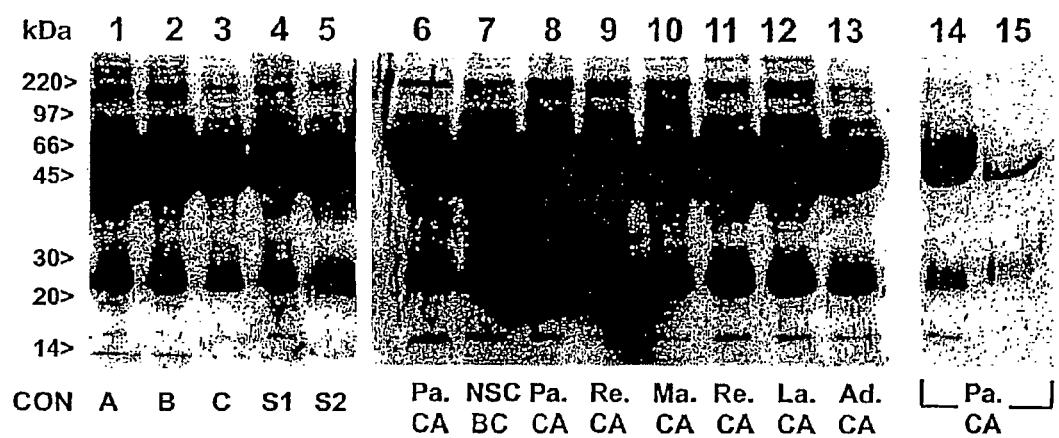
FIG. 11 shows the immunological detection of YB-1 in the serum for healthy subjects (lanes 1 to 3), for two patients with fulminant sepsis (lanes 4 and 5) and for 8 patients with metastasizing tumor diseases of different organ systems and histologies (lanes 6 to 13). In lane 14, a control reaction with the first antibody alone is applied to detect non-specific bands. In lane 15, a control reaction with the second antibody alone is applied to detect non-specific bands occurring due to the second antibody. By using a polyclonal antibody directed against the full-length YB-1 protein, the full-length YB-1 (52 kDa) and a second main band of a YB-1 fragment at 28 kDa can be detected. In addition to these YB-1 fragments, which are visible in all samples, a small YB-1 fragment having a size of about 14 kDa can be detected in all tumor patients, but only allusively in a patient with fulminant sepsis (lane 4). Thus, the detection of this fragment in a higher concentration allows the presence of a tumor disease to be concluded, without being able to attribute this result to the genesis of the tumor disease.
Figure 12:
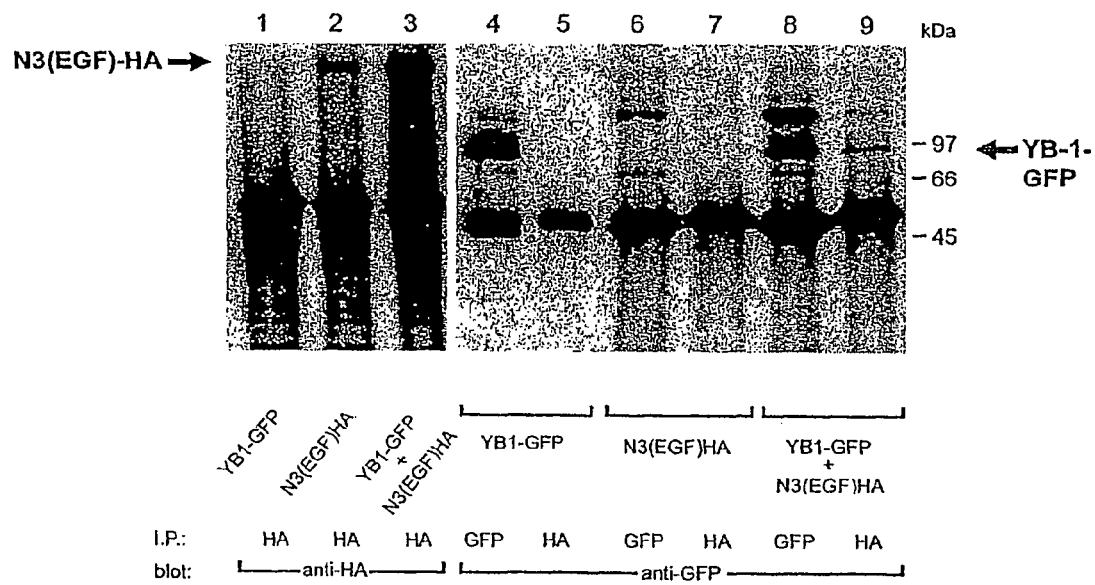
FIG. 12 shows the detection of a direct interaction of GFP-YB-1 with HA-tagged NOTCH in immunoprecipitation. For further details, see Example 10.

FIG. 11 shows the immunological detection of YB-1 in the serum of healthy subjects (lanes 1 to 3), for two patients with fulminant sepsis (lanes 4 and 5) and for 8 patients with metastasizing tumor diseases of different organ systems and histologies (lanes 6 to 13). The diagnoses include pancreatic carcinoma (Pa.-CA), non-small cell bronchial carcinoma (NSC-BC), rectal carcinoma (Re.-CA), mammary carcinoma (Ma.-CA), laryngeal carcinoma (La.-CA) and adenocarcinoma without detection of a primary tumor (Ad.-CA). In lanes 14 and 15, the samples from a tumor patient with pancreatic carcinoma are again applied. In lane 14, incubation was effected with a first antibody against YB-1, and in lane 15, incubation was effected exclusively with the second antibody to detect non-specific bands due to the second antibody. Two weak non-specific bands at 50 and 26 kDa are found. By using a polyclonal antibody directed against the full-length YB-1 protein (AB3), the full-length YB-1 (52 kDa) and a second main band of a YB-1 fragment at 28 kDa can be detected. In addition to these YB-1 fragments, which are visible in all samples, a small YB-1 fragment having a size of about 14 kDa can be detected in all tumor patients, but only allusively in a patient with fulminant sepsis (lane 4). Thus, the detection of this fragment in a higher concentration allows the presence of a tumor disease to be concluded.

Example 8

Influence of YB-1 and of Antibodies Against YB-1 on the Mobility of Keratinocytes Human keratinocytes are obtained from skin biopsies of adult donors by washing the skin samples three times with PBS solution to which penicillin and amphotericin B has been added. The samples are washed with 70% ethanol and cut to pieces of 1 cm². The epidermis is separated by incubation with caseinolytic dispase (50 U/ml, Collaborative, Bedford, Mass., USA) for 2 h at 37° C. After incubation in 0.25 mg/ml trypsin/EDTA (Cambrex, Walkersville, Md., USA) for 30 minutes at 37° C., the keratinocytes are released as a single-cell suspension by careful pipetting. After neutralizing the trypsin with trypsin neutralizing solution (TNS, Cambrex, Walkersville, Md., USA), the cells are taken up in KGM medium (Cambrex, Walkersville, Md., USA) and sown and cultured in cell culture flasks.

After confluency of the cells, a "scratch" is performed, i.e., a defect is made in the cell lawn (Draper B. K. et al., J Cell Biochem., 2003, Vol. 89, p. 1126-37). After the cells were washed with KGM medium, recombinant YB-1 or the antibodies are added in the stated concentrations.

Figure 13:
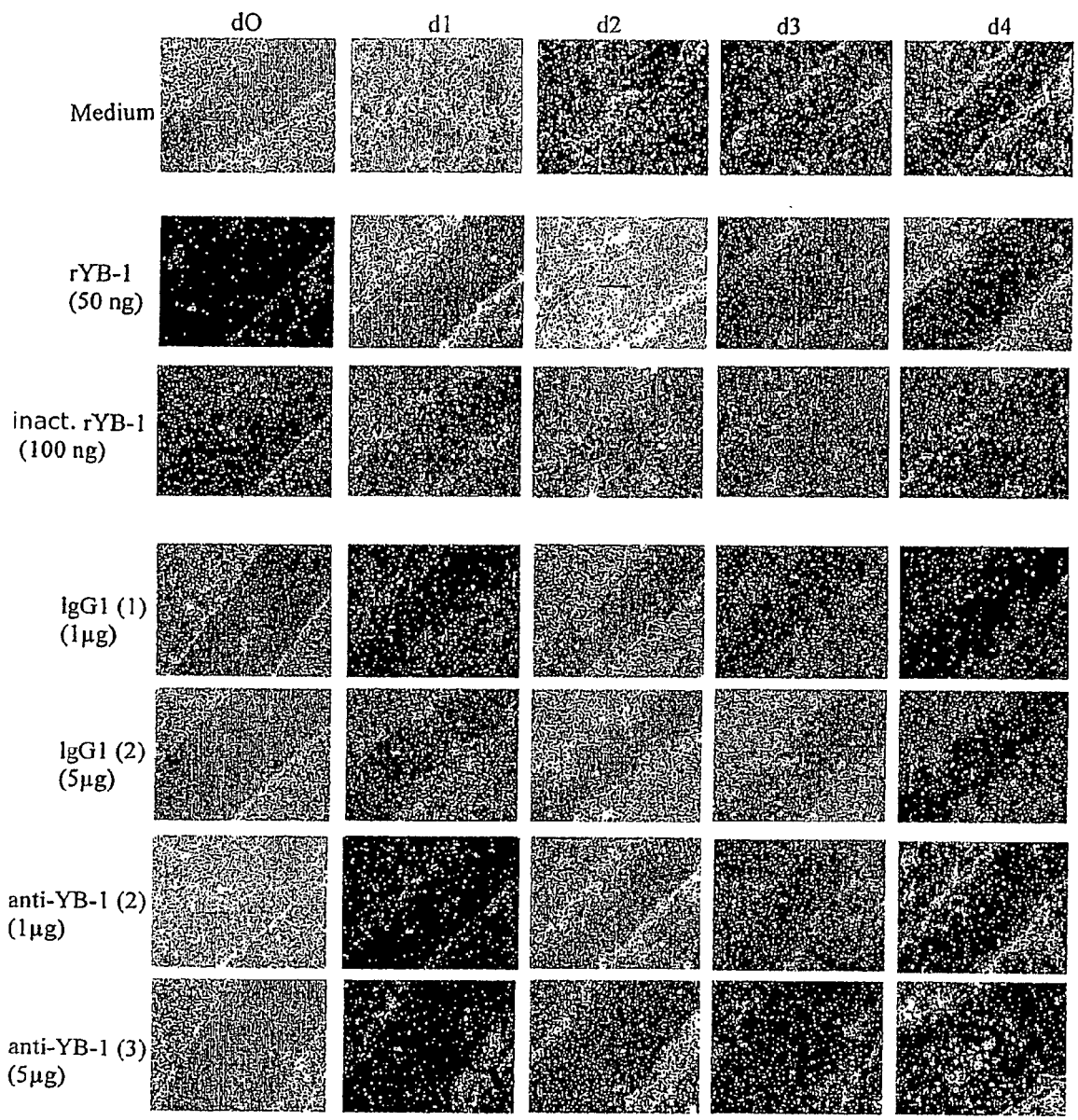
FIG. 13 shows the results of an incubation of keratinocytes with recombinant YB-1 as well as with anti-YB-1 antibodies after a scratch experiment. Line 1 with the designation "medium" shows the control incubation of the keratinocyte lawn with medium and without YB-1 or anti-YB-1 antibodies. Line 2 shows the incubation of the cell lawn with recombinant YB-1 (rYB-1 (50 ng)), line 3 shows the incubation with thermally inactivated recombinant YB-1 (rYB-1 (100 ng)), lines 4 and 5 show the incubation with the control IgG antibodies (IgG1 (1) (1 μg) and IgG1 (2) (5 μg)), and lines 6 and 7 show the incubation with anti-YB-1 antibodies (anti-YB-1 (2) (1 μg) and anti-YB-1 (3) (5 μg)). For further details, see Example 8.

Results:

The experimental results are shown in FIG. 13. While the keratinocytes immigrate into the wound produced when normal serum-free medium is added (line: medium), there is no significant immigration of the cells in the cells treated with recombinant YB-1 (line: rYB-1 (50 ng)). If the YB-1 sample expressed in bacteria is heated at 95° C. over 10 minutes and subsequently added to the keratinocyte cultures, immigration of the cells can be observed, which excludes that the inhibition effect is caused by lipopolysaccharides (line: inact. RYB-1 (100 ng)).

The addition of anti-YB-1 (line: anti-YB-1 AB4 ("Deutschland") (2) (1 µg) and anti-YB-1 (3) (5 µg)) has a similar effect on the migration of the keratinocytes, while a control IgG antibody does not influence the migration (line: IgG1 (1) (1 µg) and IgG1 (2) (5 µg)). This indicates that the monoclonal antibody employed has no neutralizing effect on the YB-1 effect, but rather enhances it.

Example 9

Detection of YB-1 Fragments by Means of Monoclonal Antibodies

Figure 10B:
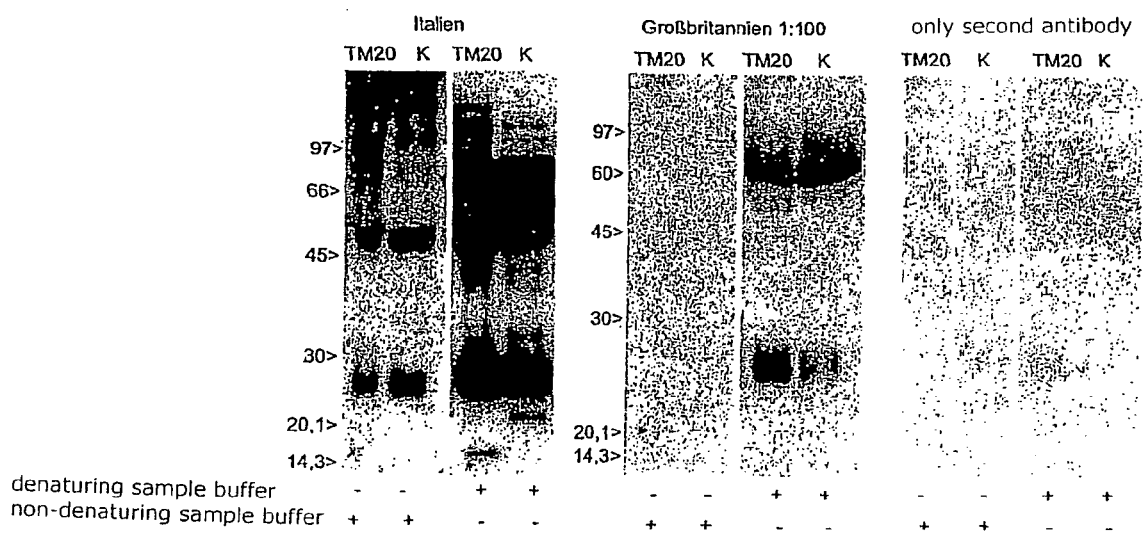
FIG. 10B shows the detection of "specific" YB-1 fragments in the serum of tumor patients and in the urine in IgA nephritis using a monoclonal antibody. For further details, see Example 9. Using the generated monoclonal antibody "Italien" (AB8, see Table 1), the serum of a tumor patient with a metastasizing rectal carcinoma (TM20) as well as urine from a patient with progredient IgA nephritis (K) were examined. In addition to high-molecular weight bands around 200 kDa, bands having relative molecular weights of 52 and 28 kDa are also observed in the non-denaturing sample buffer (without mercaptoethanol and EDTA). Under denaturing conditions (with mercaptoethanol and EDTA), the bands previously observed with different polyclonal anti-YB-1 antibodies with relative sizes of 16 kDa can be detected in the serum for a tumor disease or of 23 kDa in the urine for progredient IgA nephritis. With a control antibody without specific YB-1 binding ("Großbritannien", AB9, see Table below) and with the anti-mouse second antibody alone, the bands at 16 and 23 kDa are not detectable.

In this experiment, "specific" YB-1 fragments were detected in the serum of tumor patients and in the urine of patients with IgA nephritis by means of monoclonal antibodies (FIG. 10B). With the generated monoclonal antibody "Italien" (AB8, see Table 1), the serum of a tumor patient with metastasizing rectal carcinoma (TM20) and urine from a patient with progredient IgA nephritis (K) were examined. In addition to high-molecular weight bands around 200 kDa, bands having relative molecular weights of 52 and 28 kDa are also observed in the non-denaturing sample buffer (without mercaptoethanol and EDTA). Under denaturing conditions (with mercaptoethanol and EDTA), the bands previously observed with different polyclonal anti-YB-1 antibodies with relative sizes of 16 kDa can be detected in the serum for a tumor disease or of 23 kDa in the urine for progredient IgA nephritis. With a control antibody without specific YB-1 binding ("Großbritannien", AB9, see Table below) and with the anti-mouse second antibody (AB5) alone, the bands at 16 and 23 kDa are not detectable.

Example 10

Detection of a Direct Interaction of GFP-YB-1 with HA-Tagged NOTCH

NOTCH3 (EGF) labeled with hemagglutinin (HA) (i.e., the extracellular EGF-containing domain of the NOTCH-3 receptor) and GFP or YB-1-GFP are coexpressed in HEK293T cells. The cell lysates are subjected to immunoprecipitation with an anti-HA antibody, separated by means of SDS-PAGE and detected with the anti-HA antibody (lanes 1-3). The expressed protein N3 (EGF) can be detected in this way (lanes 2 and 3). Further, the cell lysates are respectively subjected to immunoprecipitation with an anti-GFP or the anti-HA antibody and subsequently detected by means of the anti-GFP antibody. In lane 9, co-immunoprecipitated YB-1-GFP can be seen. Corresponding control experiments in which only one of the two proteins was respectively expressed, are negative (lanes 5 and 7). "I.P." represents immunoprecipitation, and "blot" means detection by Western blotting after separation of the proteins.

What is claimed is:

1. An in vivo process for the determination of nephritis in a mammal, wherein the determination of nephritis comprises:
    examining a sample of a body fluid from said mammal for the presence of YB-1 protein and/or at least one of its fragments in said sample; and
    when YB-1 protein and/or at least one of its fragments is present in said sample, determining a secretion pattern of said YB-1 protein and its fragments in said sample, wherein the fragments are at least one fragment having a size selected from the group of: 8 kDa, 16 kDa, 23 kDa, 28 kDa, 30 kDa, 32 kDa, 35 kDa and ±5 kDa of any of the aforementioned sizes,
    wherein the presence of YB-1 and at least one of said fragments indicates that the mammal has nephritis.

2. The process according to claim 1, wherein said determination of the secretion pattern is effected by using HPLC or Western blotting.

3. The process according to claim 1, further comprising:
    correlating the secretion pattern determined with secretion patterns established from calibration series for nephritis.

4. The process according to claim 1, wherein the sample is examined for the presence of YB-1 protein and/or at least one of its fragments by means of antibodies.

5. The process according to claim 4, wherein polyclonal antibodies are used as said antibodies.

6. The process according to claim 4, wherein monoclonal antibodies are used as said antibodies.

7. The process according to claim 1, wherein a human is selected as said mammal.

8. The process according to claim 1, wherein said body fluid is at least one selected from the group comprising: blood, urine, lymph, plasma, serum, sweat, nasal secretion, vaginal secretion, wound exudate, sputum, pus, semen, stool and cerebrospinal fluid.

9. The process according to claim 8, wherein said body fluid is urine.

10. An in vivo process for the determination of a malignant disease in a mammal, wherein the determination of said malignant disease comprises:
    examining a sample of a body fluid from said mammal for the presence of YB-1 protein and/or at least one of its fragments in said sample; and
    when YB-1 protein and/or at least one of its fragments is present in said sample, determining a secretion pattern of said YB-1 protein and its fragments in said sample, wherein the fragments are at least one fragment having a size selected from the group of: 8 kDa, 16 kDa, 23 kDa, 28 kDa, 30 kDa, 32 kDa, 35 kDa and ±5 kDa of any of the aforementioned sizes,
    wherein said malignant disease is selected from the group consisting of pancreatic carcinoma, non-small cell bronchial carcinoma, rectal carcinoma, mammary carcinoma, laryngeal carcinoma, adenocarcinoma, and any combinations thereof,
    wherein the presence of YB-1 and at least one of said fragments indicates that the mammal has said malignant disease.

* * * * *